US010105171B2

(12) United States Patent
Schaus et al.

(10) Patent No.: US 10,105,171 B2
(45) Date of Patent: *Oct. 23, 2018

(54) METHOD FOR BALLOON-ASSISTED AUGMENTATION AND FUSION OF ADJACENT VERTEBRAL BODIES

(71) Applicant: Stryker Corporation, Kalamazoo, MI (US)

(72) Inventors: Erin L. Schaus, Elk Grove Village, IL (US); John A. Krueger, Muskego, WI (US); Ellen Ehrich Kourakos, Chicago, IL (US); Amy E. Ewing, Buffalo Grove, IL (US)

(73) Assignee: STRYKER CORPORATION, Kalamazoo, MI (US)

( * ) Notice: Subject to any disclaimer, the term of this patent is extended or adjusted under 35 U.S.C. 154(b) by 151 days.

This patent is subject to a terminal disclaimer.

(21) Appl. No.: 15/183,206

(22) Filed: Jun. 15, 2016

(65) Prior Publication Data
US 2016/0287303 A1 Oct. 6, 2016

Related U.S. Application Data

(63) Continuation of application No. 14/215,863, filed on Mar. 17, 2014, now Pat. No. 9,393,061.

(51) Int. Cl.
A61B 17/88 (2006.01)
A61B 17/34 (2006.01)
(Continued)

(52) U.S. Cl.
CPC ...... A61B 17/8805 (2013.01); A61B 17/3472 (2013.01); A61B 17/56 (2013.01);
(Continued)

(58) Field of Classification Search
CPC ... A61B 17/56; A61B 2017/564; A61B 17/88; A61B 17/8802; A61B 17/8805;
(Continued)

(56) References Cited

U.S. PATENT DOCUMENTS 6,558,390 B2    5/2003   Cragg
6,805,697 B1 *  10/2004  Helm ................. A61B 17/1671
                                                606/92
(Continued)

FOREIGN PATENT DOCUMENTS

WO    WO 2013180947 A1    12/2013

OTHER PUBLICATIONS

CareFusion Corporation, "AVAmax Advanced Vertebral Augmentation system—A 21st century appraoch to vertebral augmentation," 2011, 24 pages, CareFusion, Waukegan, IL.
(Continued)

Primary Examiner — Larry E Waggle, Jr.
(74) Attorney, Agent, or Firm — Howard & Howard Attorneys PLLC

(57) ABSTRACT

A vertebral augmentation system and methods for vertebral augmentation and/or fusion using same are provided. In certain embodiments, a pre-curved stylet or needle with an overlying delivery tube may be used to target a site within a bone structure, facilitating direction thereto of an expandable member useful for creating a cavity that may receive curable material to restore bone height, to reinforce the bone structure, and/or to fuse two, three, or more adjacent vertebrae. An expandable member such as, for example, a balloon can be used to create a plurality of voids by displacing bone material, where the voids can be filled with curable material to augment the vertebrae and intervening space can be filled to fuse those adjacent vertebrae.

18 Claims, 19 Drawing Sheets

(51) Int. Cl.
*A61F 2/44* (2006.01)
*A61B 17/56* (2006.01)

(52) U.S. Cl.
CPC .......... *A61B 17/88* (2013.01); *A61B 17/8802* (2013.01); *A61B 17/8811* (2013.01); *A61B 17/8816* (2013.01); *A61B 17/8819* (2013.01); *A61B 17/8855* (2013.01); *A61F 2/4455* (2013.01); *A61B 2017/564* (2013.01)

(58) Field of Classification Search
CPC ............ A61B 17/8811; A61B 17/8816; A61B 17/8819; A61B 17/8855; A61B 17/34; A61B 17/3472
See application file for complete search history.

(56) References Cited

U.S. PATENT DOCUMENTS

| | | | |
|---|---|---|---|
| 7,166,110 B2 | 1/2007 | Yundt | |
| 7,241,297 B2* | 7/2007 | Shaolian | A61B 17/1617 606/170 |
| 7,713,273 B2 | 5/2010 | Krueger et al. | |
| 7,799,035 B2 | 9/2010 | Krueger et al. | |
| 7,922,690 B2 | 4/2011 | Plishka et al. | |
| 8,128,633 B2 | 3/2012 | Linderman et al. | |
| 8,226,657 B2 | 7/2012 | Linderman et al. | |
| 8,277,506 B2 | 10/2012 | Krueger et al. | |
| 8,357,197 B2* | 1/2013 | McGraw | A61B 17/70 606/329 |
| 8,357,198 B2 | 1/2013 | McGraw et al. | |
| 9,095,393 B2 | 8/2015 | Schaus et al. | |
| 9,101,408 B1* | 8/2015 | Dix | A61B 17/7083 |
| 9,393,061 B2* | 7/2016 | Schaus | A61B 17/8805 |
| 2006/0195091 A1 | 8/2006 | McGraw et al. | |
| 2006/0195094 A1 | 8/2006 | McGraw et al. | |
| 2010/0087828 A1 | 4/2010 | Krueger et al. | |
| 2012/0239047 A1 | 9/2012 | Linderman et al. | |
| 2013/0012951 A1* | 1/2013 | Linderman | A61B 17/1642 606/93 |

OTHER PUBLICATIONS

CareFusion Corporation, "AVAflex vertbral balloon system," 2014, 2 pages, CareFusion, Vernon Hills, IL.
International Search Report for PCT/US2015/014412 dated May 20, 2015, 5 pages.

* cited by examiner

METHOD FOR BALLOON-ASSISTED AUGMENTATION AND FUSION OF ADJACENT VERTEBRAL BODIES

CROSS REFERENCE TO RELATED APPLICATIONS

This application claims priority as a Continuation under 35 U.S.C. § 120 of U.S. patent application Ser. No. 14/215,863, entitled "METHOD FOR BALLOON-ASSISTED AUGMENTATION AND FUSION OF ADJACENT VERTEBRAL BODIES," filed Mar. 17, 2014, which is incorporated by reference herein in its entirety.

TECHNICAL FIELD

Embodiments disclosed herein generally relate to methods for stabilizing and/or connecting bone structures. More particularly, they relate to systems and methods for accessing and delivering curable material across a plurality of adjacent vertebral bodies to augment and/or fuse those bodies.

BACKGROUND

Surgical intervention of damaged or compromised bone sites has proven highly beneficial for patients, including, for example, patients with back pain associated with vertebral body damage. The vertebral damage may be due to injury and/or a degenerative condition such as, for example, aging and/or osteoporosis. The damage associated with these conditions may also affect long bones, the pelvis, and other bones. Compression fractures of the vertebrae may have direct impact on spinal nerves, causing pain and other impairment.

Bones of the human skeletal system include mineralized tissue that may be generally categorized into two morphological groups: "cortical" bone and "cancellous" bone. Outer walls of all bones are composed of cortical bone, which is a dense, compact bone structure characterized by a microscopic porosity. Cancellous or "trabecular" bone forms the interior structure of bones. Cancellous bone is composed of a lattice of interconnected slender rods and plates known by the term "trabeculae".

During certain bone-related procedures, cancellous bone is supplemented by an injection of a palliative (or curative) material employed to stabilize the trabeculae. For example, superior and inferior vertebrae in the spine may be beneficially stabilized by the injection of an appropriate, curable material (e.g., PMMA or other bone cement or bone curable material). In other procedures, percutaneous injection of stabilization material into vertebral compression factors, by, for example, transpedicular or parapedicular approaches, has proven beneficial in relieving pain and stabilizing damaged bone sites. Such techniques are commonly referred to as vertebroplasty, or when implemented with a balloon, as kyphoplasty. In certain cases, vertebral augmentation may not alleviate targeted symptoms, and a spinal fusion procedure may be implemented to align the vertebrae in a manner intended to treat, and alleviate pain and other symptoms associated with, vertebral compression fractures.

A conventional vertebroplasty technique for delivering the bone stabilizing material entails placing a cannula with an internal trocar into the targeted delivery site, generally conducted in a bipedicular manner (i.e., via two pedicles of a vertebra, each of which is located as a thinner portion of cortical bone between the central spinous process and one of the transverse processes of a given vertebra). The cannula and trocar are used in conjunction to pierce the cutaneous layers of a patient above the hard tissue to be supplemented, then to penetrate the hard cortical bone of the vertebra, and finally to traverse into the softer, cancellous bone underlying the cortical bone. After the assembly is positioned in the cancellous bone, the trocar may be removed, leaving the cannula in the appropriate position for delivery of curable material that will reinforce and solidify the target site.

In spinal fusion procedures, metal plates and/or rods are typically attached to two or more adjacent vertebrae by metal screws. Bone graft material may be used to augment the fusion process. Recovery is often more time-consuming and intensive than for vertebroplasty or kyphoplasty. Spinal fusion may be used to treat other conditions including spinal stenosis, disc injuries and degeneration, trauma, infection, and tumors.

There exists a need in the medical device field for improved systems and methods for fusing adjacent vertebrae. In particular, it would be desirable to provide apparatus and methods to provide a fusion method that provides bone augmentation to stabilize vertebrae.

It may be desirable to provide a system and method that provides advantages with regard to reduced complexity, reduced procedure time, and reduced recovery time and patient pain, while maintaining advantages known from kyphoplasty offering a further advantage of a single and/or smaller surgical wound sites rather than those associated with traditional spinal fusion procedures.

BRIEF SUMMARY

In one aspect, embodiments disclosed herein may include a method of balloon-aided vertebroplasty modified to provide a spinal fusion of adjacent vertebrae. In certain embodiments, one or more needles may be used to target an approximately centered target site within adjacent vertebrate, facilitating direction thereto of an expandable member useful for creating one or more cavities that may receive curable material to reinforce the bone structure and/or provide fusion. The expandable member may be constrained by an outer tube during certain method steps, and exposed therefrom for other method steps, during which the expandable member may be inflated to create one or more cavities.

DETAILED DESCRIPTION

Figure 1:
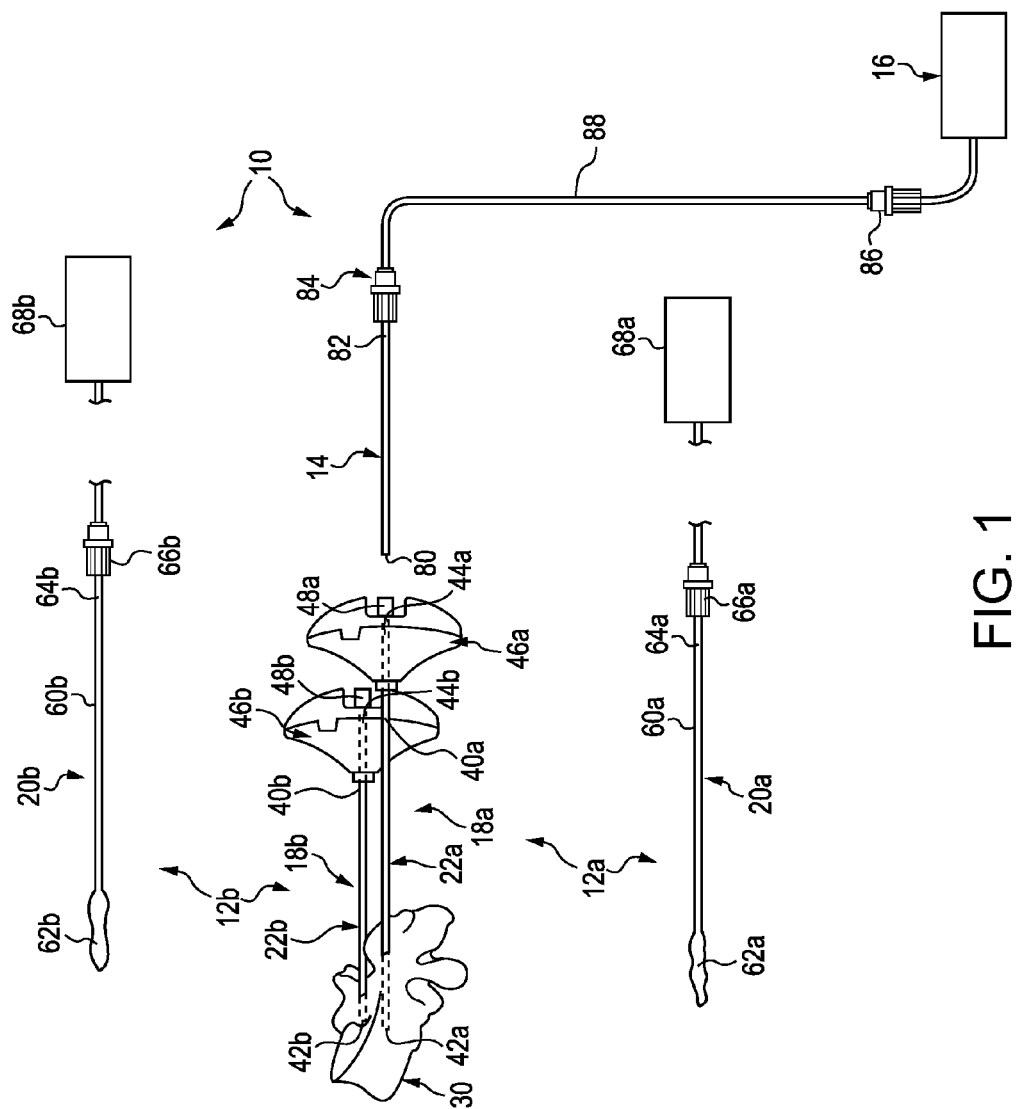
FIG. 1 is an exploded view of curable material delivery, using apparatus for bipedicular access.
Figure 2A:
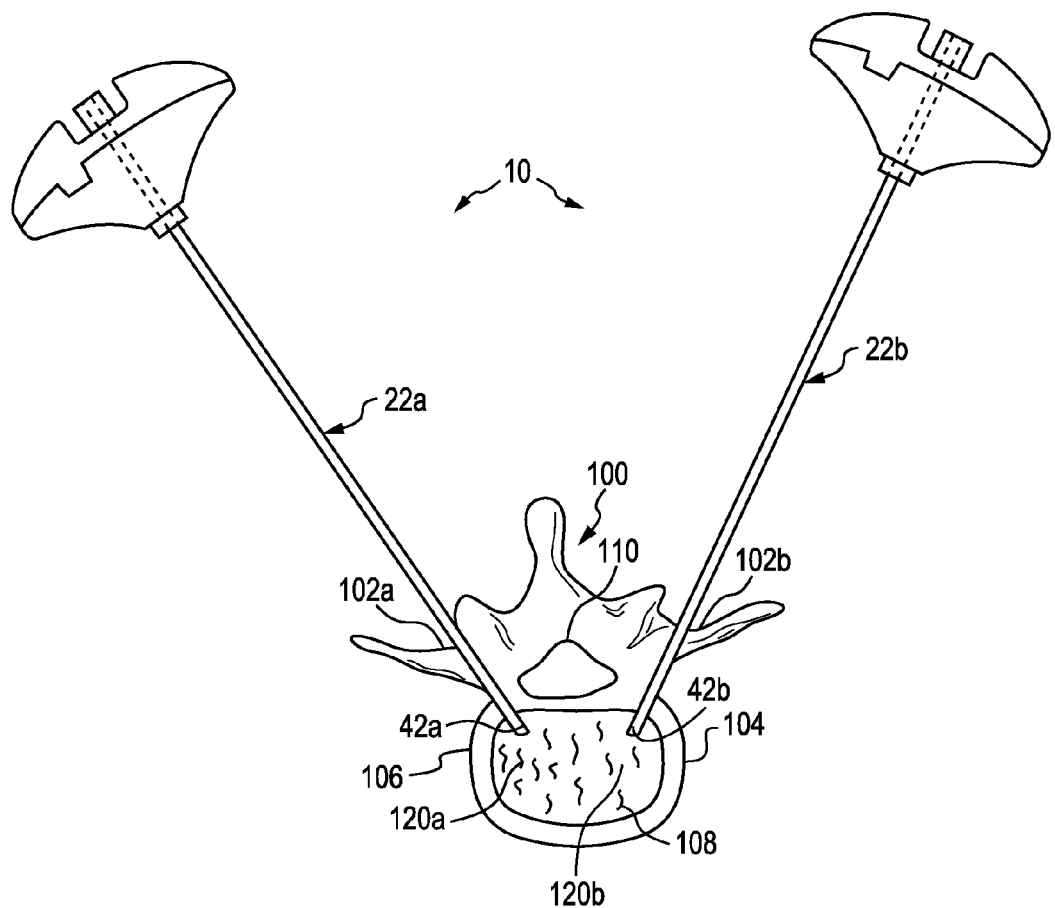
FIGS. 2A and 2B illustrate use of the system of FIG. 1 in performing a curable material delivery procedure relative to a vertebra, with the vertebra being shown from a superior perspective.
Figure 2B:
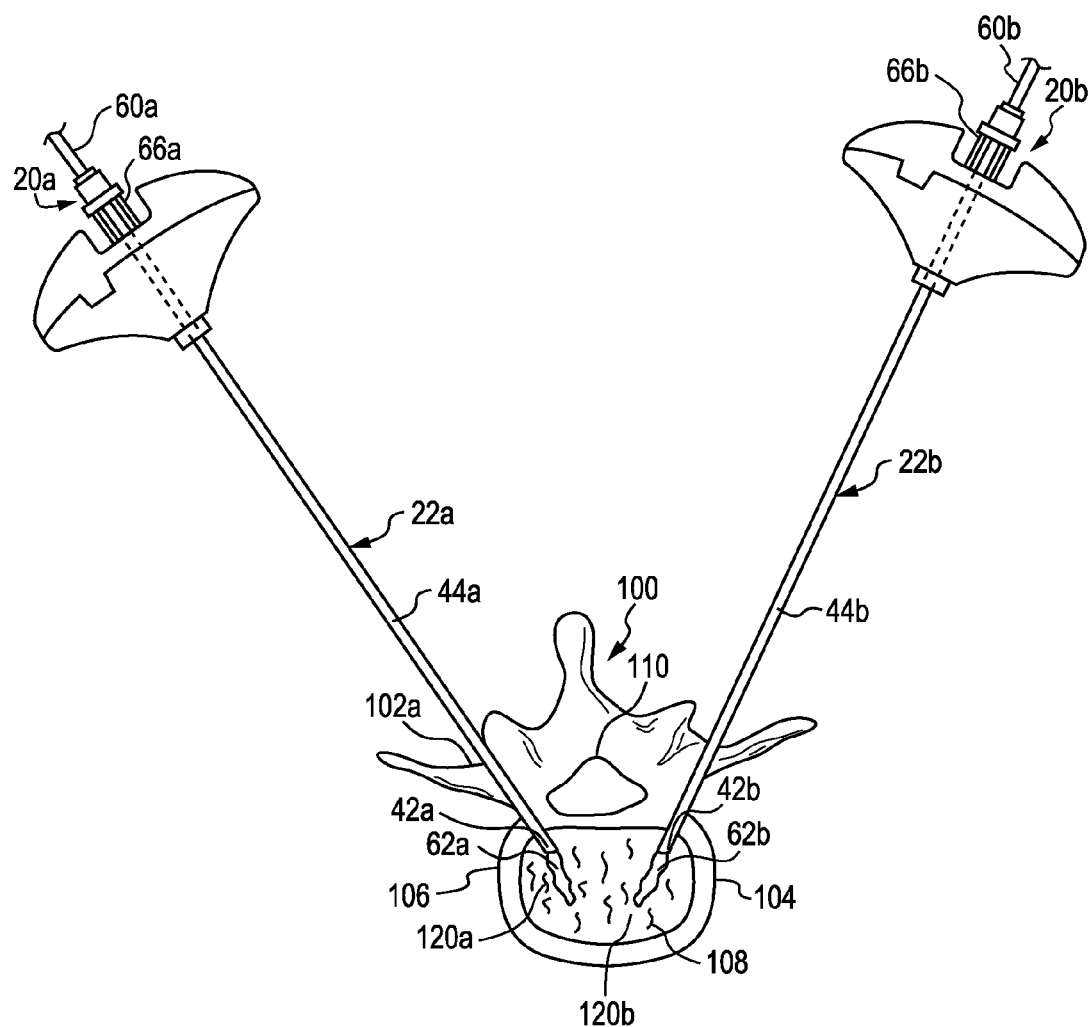

Embodiments are described with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly. Specifically, with reference to scale, the proportion of wall thickness to lumen size and other components shown is not drawn to scale in many of the embodiments illustrated herein. Throughout the specification, the terms "distal" and "distally" shall denote a position, direction, or orientation that is generally away from the physician (including any other person holding/operating a device) and/or toward a treatment zone/patient. Accordingly, the terms "proximal" and "proximally" shall denote a position, direction, or orientation that is generally towards the physician.

Various embodiments will be described more fully hereinafter. The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. The word "alternatively" and its variants are used inclusively rather than exclusively (i.e., "X, alternatively, Y" means "X and/or Y" rather than "only X or only Y") unless otherwise apparent.

Currently, balloon assisted vertebral augmentation procedures typically are performed using a bipedicular approach, which allows internal cavities to be created on both sides of a single vertebral body. Cement is then injected into both halves of the vertebral body through each of the pedicles or through one pedicle using a curved needle system, such as, for example, an AVAflex® system (CareFusion Corp., San Diego, Calif.). The proposed method uses a device such as disclosed herein (with reference to FIGS. 1-4H, which provide procedural access in a manner known for vertebroplasty and kyphoplasty). Those figures describe how to introduce a balloon, which can—in other method steps—be inflated across a plurality of vertebral bodies. As such, FIGS. 1-4H provide teaching of balloon kyphoplasty methods that can be implemented or augmented in keeping with principles of spinal-fusion methods of the present disclosure, certain embodiments of which methods are illustrated in and described with reference to FIGS. 5A-8D.

The present procedure allows a physician to perform targeted balloon placement using the flexible, curved end and tip of a needle within an overlying delivery tube to form a passage in which to expand the balloon. In a kyphoplasty procedure, it is often ideal to inflate a balloon through a single access point in a vertebral body to keep the procedure as minimally invasive as possible and minimize trauma to the pedicles. Knowing that vertebral bodies may be large compared to standard balloon lengths, there may be advantages to using this device with the present method, including advantages for accessing and fusing adjacent vertebrae.

After inflating the balloon in a targeted area (which may be across/opposite the midline from the introducing/puncture site), the balloon may be retracted along the same pathway and re-inflated to create a larger cavity or two distinct cavities within a single vertebral body. This may provide certain advantages, because it can also provide a continuous cavity for cement containment across adjacent vertebrae to fuse them together.

One embodiment of a curable material delivery system 10 is shown in FIG. 1. The system 10 includes a first delivery assembly 12a, a second delivery assembly 12b, and at least one curable material source 16. The delivery assemblies 12a, 12b may be substantially identical, and each includes a cannula device 18a, 18b and a cavity-forming device 20a, 20b. Details on the various components are provided below. In general terms, however, the cannula devices 18a, 18b each include an access cannula 22a, 22b for insertion into a bone site of interest in a patient. In the embodiment depicted in FIG. 1, the bone site of interest is a vertebra 30. After the access cannulas 22a, 22b are desirably located relative to the vertebra 30, a portion of each of the cavity-forming devices 20a, 20b are delivered to the vertebra 30 via the corresponding access cannula 22a, 22b, and operated to form cavities. The second cavity-forming device 20b (alternatively the first cavity-forming device 20a) may be removed, and the curable material source 16 connected to the second cannula 22b. In this regard, a delivery tube 14 may be employed, extending from the source 16 and through the second cannula 22b.

Thereafter, the curable material source 16 is operated to deliver curable material to the cavity via the second cannula 22b and/or the delivery tube 14. Subsequently, the first cavity-forming device 20a may be removed and the curable material source 16 is connected to the first cannula 22a (for example, via the delivery tube 14). The curable material source 16 is operated to deliver curable material into the corresponding cavity. With the approaches disclosed herein, the systems and methods disclosed herein and the delivered curable material will provide desirable stabilization for a patient's spine.

The system 10 may be used for a number of different procedures including, for example, vertebroplasty and other bone augmentation procedures in which curable material is delivered to a site within bone, as well as possibly to remove or aspirate material from a site within bone. The system 10 is highly useful for delivering a curable material in the form of a bone curable material. The phrase "curable material" within the context of the substance that may be delivered by the systems and methods described herein is intended to refer to materials (e.g., composites, polymers, and the like) that have a fluid or flowable state or phase and a hardened, solid or cured state or phase.

Curable materials may include, but are not limited to, injectable bone cements (such as polymethylmethacrylate (PMMA) bone curable material), which have a flowable state wherein they may be delivered (e.g., injected) by a cannula to a site and subsequently cure into hardened, cured material. Other materials such as calcium phosphates, bone in-growth materials, antibiotics, proteins, etc., may be used in place of, or to augment bone cement (but do not affect an overriding characteristic of the resultant formulation having a flowable state and a hardened, solid, or cured state). This would allow the body to reabsorb the curable material and/or improve the clinical outcome based on the type of filler implant material. Although FIG. 1 illustrates a single curable material source 16, in other embodiments, two (or more) sources may be provided. The sources may contain identical curable material compositions; alternatively, the compositions may differ (e.g., a first source may contain bone cement, while a second source contains a mixture of bone cement and bone in-growth material).

As mentioned above, the cannula devices 18a, 18b may be substantially identical, and each includes the outer/access cannula 22a, 22b. The cannula 22a, 22b is provided to be positioned in (or immediately proximate) the target or injection site for delivery of the corresponding cavity-forming device 20a, 20b, as well as curable material. The cannula 22a, 22b preferably is made of a surgical grade of stainless steel, but may be made of known equivalent material(s) that are both biocompatible and substantially non-compliant at the expected operating pressures. The cannulas 22a, 22b each define a proximal region 40a, 40b, a distal end 42a, 42b, and a lumen 44a, 44b (referenced generally), respectively, to allow various equipment such as the cavity-forming device 20a, 20b, a delivery tube 14, one or more needles (not shown here, but discussed and illustrated with reference to embodiments of FIGS. 4A-4H below), and/or other elements, to pass therethrough.

A handle 46a, 46b surrounds the proximal region 40a, 40b of the cannula 22a, 22b for manipulating the cannula 22a, 22b and for connecting the cannula 22a, 22b with one or more of the cavity-forming device 20a, 20b and/or the delivery tube 14. In some constructions, the cannula device 18a, 18b may further include a handle connector 48a, 48b serving as a proximal end of the corresponding cannula 22a, 22b. The handle connector 48a, 48b may simply be an extension of the cannula 22a, 22b. Alternatively, the handle connector 48a, 48b may incorporate features forming part of a locking mechanism component of the system 10. For example, the handle connector 48a, 48b may include a luer-lock type of connector, but other known connecting mechanism may be successfully interchanged (e.g., a conventional threaded hole, a threaded locking nut arrangement, etc.). Features of one suitable locking mechanism are described in U.S. Pat. No. 7,922,690, which is incorporated herein by reference in its entirety.

The cavity-forming devices 20a, 20b may be substantially identical and may assume various forms appropriate for forming a void or cavity within bone. In this regard, each of the cavity-forming devices 20a, 20b includes an elongated body 60a, 60b distally connected to or forming a working end 62a, 62b. The elongated body 60a, 60b is sized to be slidably inserted within the lumen 44a, 44b of the corresponding cannula 22a, 22b, and may include one or more tubes, shafts, etc., necessary for operation of the corresponding working end 62a, 62b. Thereafter, a proximal region 64a, 64b of the elongated body 60a, 60b may be connected to or form a cannula connector 66a, 66b. The cannula connector 66a, 66b may assume various forms conducive for selective, rigid attachment to the corresponding handle connector 48a, 48b as described above (e.g., the cannula connector 66a, 66b and the corresponding handle connector 48a, 48b collectively form a locking mechanism), and thus may include or contain a luer-lock threaded fitting. Alternatively, the cannula connector 66a, 66b may be omitted, and depth markings (not shown) included along an exterior of the proximal region 64a, 64b that facilitate desired locating of the working end 62a, 62b relative to the corresponding cannula 22a, 22b as described below.

The working end 62a, 62b may include one or more components appropriate for forming a cavity or void within bone. For example, in some constructions, the working end 62a, 62b may include one or more expandable or inflatable members (e.g., a single balloon, multiple balloons, a single balloon with two or more discernable inflation zones, etc.) constructed to transition between a contracted (e.g., deflated) state in which the working end/balloon 62a, 62b may be passed through the corresponding lumen 44a, 44b, and an expanded (e.g., inflated) state in which the working end/balloon 62a, 62b expands and compacts contacted cancellous bone. In this regard, a size and shape of the working end/balloon 62a, 62b may be predetermined and/or restrained with one or more additional components (not shown), such as internal and/or external restraints. In preferred embodiments the working end/balloon 62a, 62b will be structurally robust, able to withstand (e.g., not burst) at expected inflation pressures and when in contact with bone. Further, the first working end 62a and the second working end 62b may be identical or different.

The working ends/balloons 62a, 62b may be exteriorly coated with a material configured to resist bonding with the curable material being delivered to the vertebra 30. The anti-sticking coating may assume various forms as a function of the selected curable material, and in some embodiments is a silicone coating. Other materials exhibiting aversion to bonding with bone cement are also envisioned, for example, polypropylene. In related embodiments, a thin-walled expandable sleeve constructed of the selected anti-sticking material (e.g., a polypropylene sleeve) may be disposed over the working end/balloon 62a, 62b. Though not shown, one or both of the cavity-forming devices 20a, 20b may include a valve or similar component that operates to selectively seal the working end/balloon 62a, 62b.

The cavity-forming devices 20a, 20b each further include one or more additional components connected or operable through the proximal region 64a, 64b for actuating the corresponding working end 62a, 62b. By way of one non-limiting example, each of the cavity-forming devices 20a, 20b may include a source 68a, 68b of pressurized fluid (e.g., contrast medium) for inflating the balloon(s) carried or formed by the corresponding working end 62a, 62b. A hand-held, syringe-type pump may be used as the pressurized source. In other embodiments, a single one of the pressurized fluid sources 68a or 68b may be provided and employed to inflate both of the working ends/balloons 62a, 62b individually. Appropriate balloon-inflation systems are well known and will readily be apparent to those of skill in the art.

Where provided, the delivery tube 14 is sized for insertion within the lumens 44a, 44b, and defines a distal tip 80 and a proximal section 82. As described below, the delivery tube 14 may be employed to deliver curable material to the target site. Thus, the delivery tube 14 has an outer diameter that is smaller than a diameter of the lumens 44a, 44b; however, the outer diameter of the delivery tube 14 preferably will not be so small as to allow curable material to readily travel around the outside of the delivery tube 14 and back into the corresponding cannula 22a, 22b.

A cannula connector 84 may be coupled to, or formed by, the proximal section 82 of the delivery tube 14. The cannula connector 84 is akin to the cannula connector 66a, 66b described above (e.g., combines with the selected handle connector 48a, 48b to form a locking mechanism), and thus may assume any of the forms previously described. Alternatively, the delivery tube 14, where provided, may form depth markings (not shown) along the proximal section 82 that facilitates desired locating of the distal tip 80 relative to the cannula 22a, 22b during use.

The delivery tube 14 is configured for fluid coupling to the curable material source 16. In some embodiments, a portion of the delivery tube 14 projects proximally beyond the cannula connector 84, and is fluidly coupled to the curable material source 16, for example via an injection connector 86. Alternatively, auxiliary tubing 88 may be provided with the curable material source 16, and fluidly connected to the delivery tube 14 via the cannula connector 84. In yet other embodiments, the delivery tube 14 is omitted, and the curable material source 16 connected directly to the handle connector/proximal end 48a, 48b (e.g., the auxiliary tube 88 is connected to the connector 48a, 48b; or the auxiliary tube 88 may be eliminated and the curable material source 16 (e.g., a syringe) directly coupled to the connector 48a, 48b).

The curable material source 16 may assume various forms appropriate for delivering the desired curable material, and may typically comprise a chamber filled with a volume of curable material and employing any suitable injection system or pumping mechanism to transmit curable material out of the chamber and through the delivery tube 14. Typically, a hand injection system is used where a user applies force by hand to an injector. The force is then translated into pressure on the curable material to flow out of the chamber. A motorized system may also be used to apply force.

Although the system 10 has been described as including the single curable material source 16, in other constructions, a separate curable material source 16 may be provided for each of the delivery assemblies 12a, 12b. Similarly, two (or more) of the delivery tubes 14 may be included. Along these same lines, the system 10 may be configured such that the curable material source 16 is directly connected to one or both of the cavity-forming devices 20a, 20b (e.g., the elongated body 60a of the first cavity-forming device 20a may form or terminate at a nozzle proximate (e.g., distal) the working end 62a and through with the curable material may be directly dispensed).

FIGS. 2A-3B illustrate use of the system 10 in delivering curable material into, a target site of a vertebra 100. In general terms, the vertebra 100 includes pedicles 102a, 102b and a vertebral body 104 defining a vertebral wall 106 surrounding bodily material 108 (e.g., cancellous bone, blood, marrow, and soft tissue). The pedicles 102a, 102b extend from the vertebral body 104 and surround a vertebral foramen 110. As a point of reference, systems of the present disclosure may be suitable or readily adapted by those of skill in the art for accessing a variety of bone sites. Thus, although the vertebra 100 target site is illustrated, it is to be understood that other bone sites may be accessed and treated by the system 10 (e.g., femur, long bones, ribs, sacrum, etc.).

The first and second cannulas 22a, 22b may be employed to form first and second access paths to first and second target site locations 120a, 120b. For example, the cannulas 22a, 22b are inserted in a bipedicular fashion through respective ones of the pedicles 102a, 102b and into the bodily material 108. The cannulas 22a, 22b provide access to the corresponding target site 120a, 120b at the open distal ends 42a, 42b thereof. One or more needles (not shown) may be employed to assist in forming/accessing the target sites 120a, 120b. For example, a series of differently-sized or configured (e.g., sharpened and blunt) needles may be successively delivered through the respective cannula 22a, 22b to form a channel to the target site 120a, 120b. Alternatively, or in addition, an outer guide cannula (not shown) may be deployed to form an access path for subsequent insertion of the cannulas 22a, 22b.

After the cannulas 22a, 22b are positioned within the bodily material 108 at the desired target sites 120a, 120b, the cavity-forming devices 20a, 20b are assembled to the corresponding cannula 22a, 22b. For example, and as shown in greater detail in FIG. 2B, the elongated body 60a, 60b is slidably inserted within the corresponding cannula 22a, 22b, with the respective working end 62a, 62b being distally advanced therethrough. More particularly, with configurations in which the working end 62a, 62b is a balloon or other expandable member format, the working end/balloon 62a, 62b is transitioned to a contracted state (e.g., deflated) so as to be slidably received through the lumen 44a, 44b. The elongated body 60a, 60b is positioned relative to the corresponding cannula 22a, 22b such that the respective working end/balloon 62a, 62b extends distal the corresponding cannula distal end 42a, 42b. For example, where the elongated body 60a, 60b may include depth markings as described above, the appropriate depth marking will be aligned with the corresponding handle connector 48a, 48b (FIG. 1), thereby ensuring that the working end/balloon 62a, 62b is fully deployed or extended beyond the corresponding cannula distal end 42a, 42b. In other constructions, upon connection of the cannula connector 66a, 66b and the corresponding handle connector 48a, 48b, the working end/balloon 62a, 62b is distal the corresponding distal end 42a, 42b and is positioned at the corresponding target site 120a, 120b. Placement of the cavity-forming devices 20a, 20b may be performed simultaneously or consecutively.

Figure 3A:
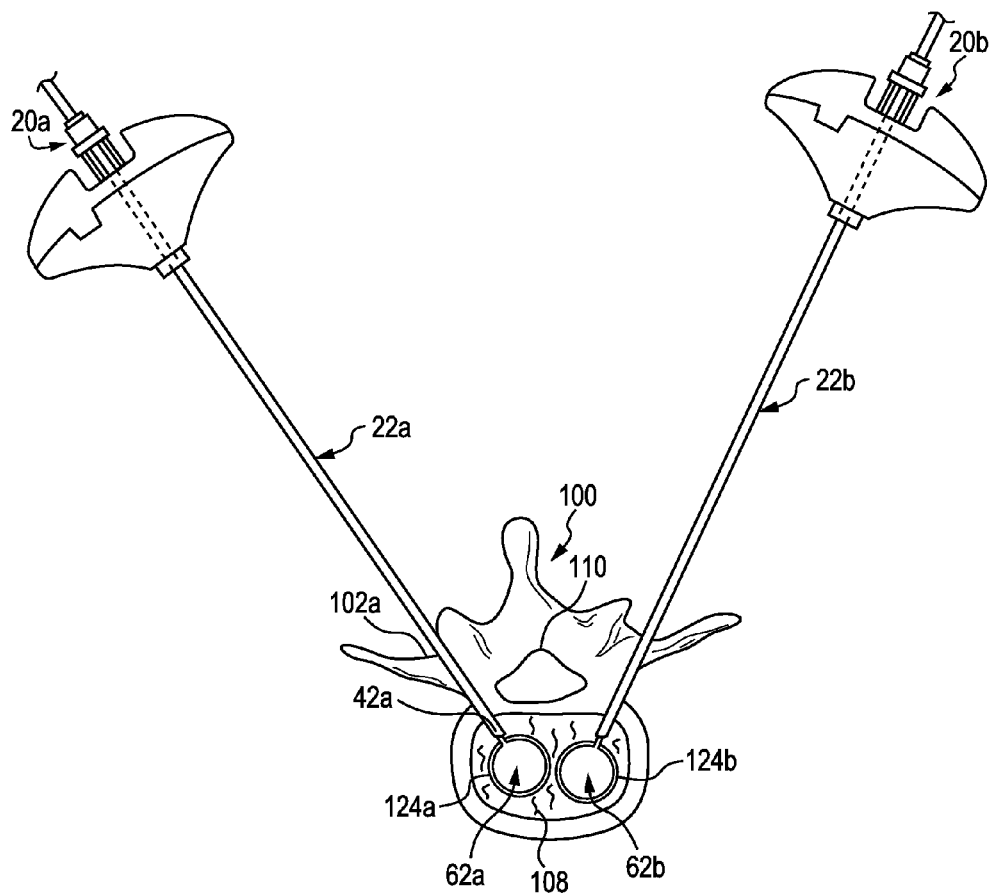
FIGS. 3A-3B illustrate the system of FIG. 1 in further performing a curable material delivery procedure with a bipedicular dual-balloon method.
Figure 3B:
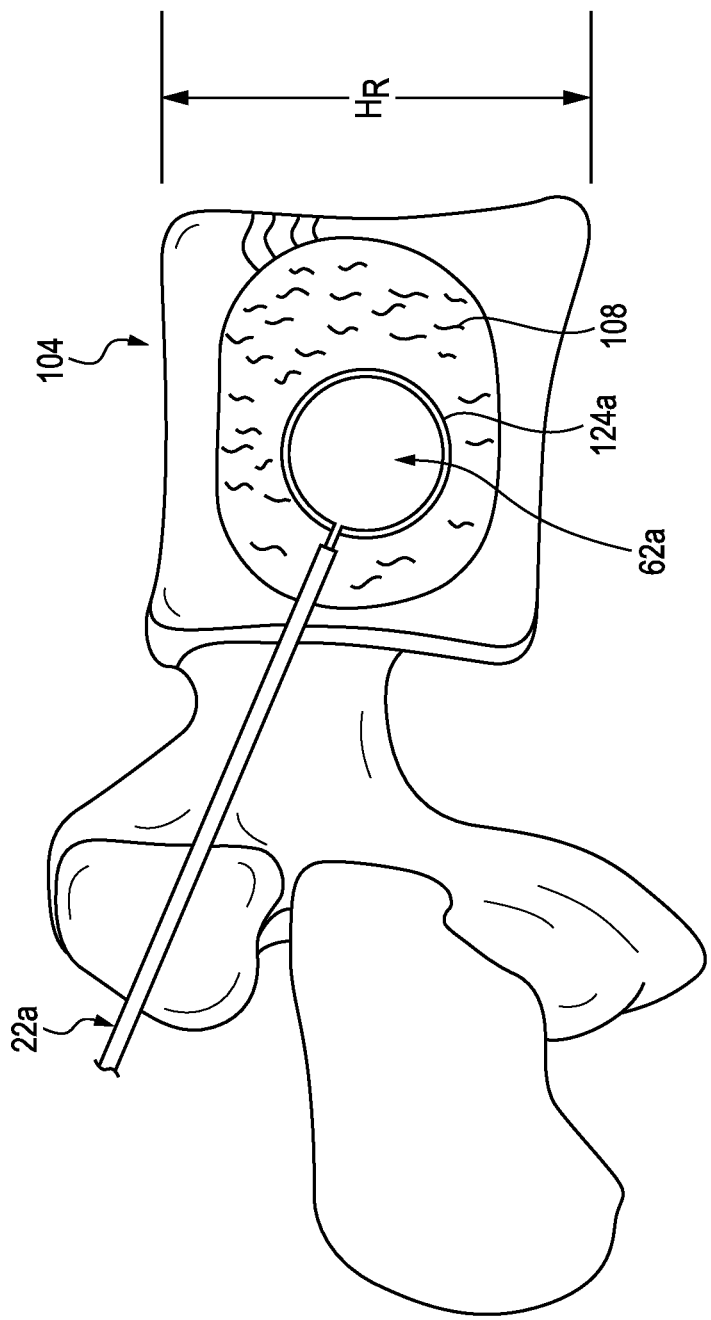

With reference to FIG. 3A, the cavity-forming devices 20a, 20b are operated to cause the corresponding working ends/balloons 62a, 62b to form first and second cavities or voids 124a, 124b, respectively, in the bodily material 108. For example, the working ends/balloons 62a, 62b may be expanded (e.g., inflated) substantially simultaneously. Alternatively, with embodiments in which a single inflation/pressurized fluid source 68a or 68b (FIG. 1) is provided, the first working end/balloon 62a is inflated and then sealed in the expanded or inflated state. The inflation/pressurized fluid source 68a or 68b is then fluidly connected to the second working end/balloon 62b and operated to cause expansion thereof. Following expansion of the working ends/balloons 62a, 62b, the expanded working ends/baloons 62a, 62b are both supporting the vertebral body 104. In this regard, and as best illustrated in FIG. 3B, expansion of the working ends/balloons 62a, 62b not only forms the cavities 124a, 124b, but also restores or enhances a height $H_R$ of the fractured vertebral body 104.

Returning to FIG. 3A, the second cavity-forming device 20b is then operated to transition the second working end/balloon 62b from the expanded state to the contracted state (e.g., the second balloon 62b is deflated). In the contracted state of the second working end/balloon 62b, the second cavity-forming device 20b may be removed from the second cannula 22b.

Figure 4A:
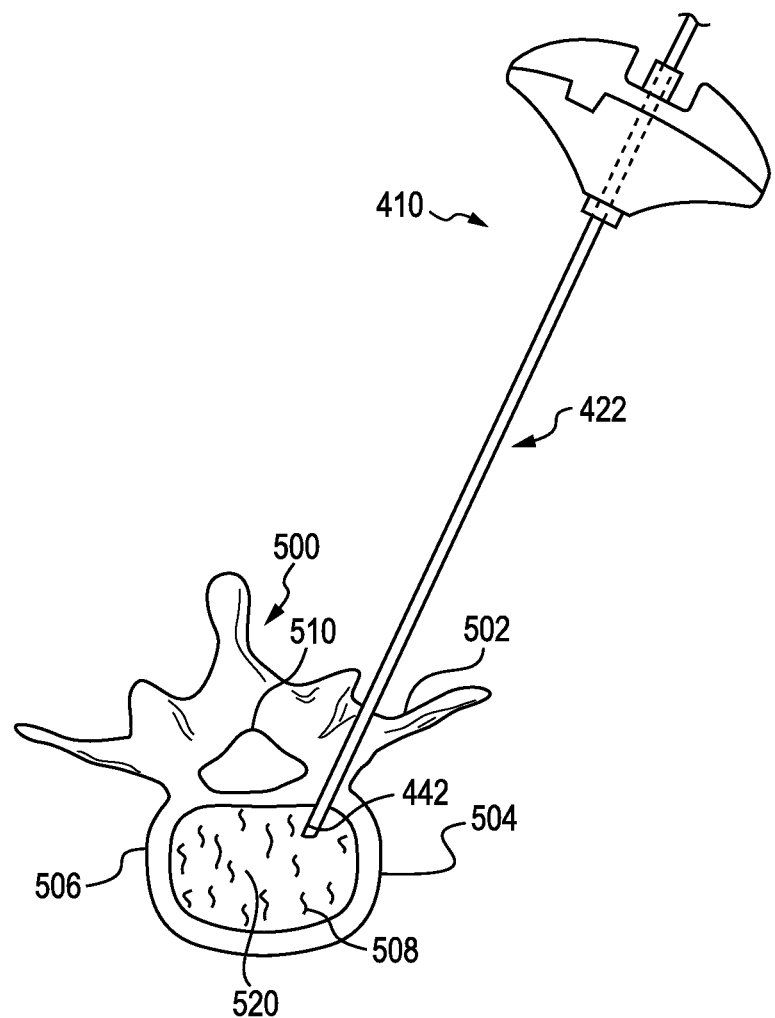
FIGS. 4A-4H illustrate a system and method for transpedicular or parapedicular access providing stylet-guided, generally centralized location of a cavity/void and curable material placement therein.

Other embodiments of a system and method for bone augmentation are described with reference to FIGS. 4A-4D. A system 410 is illustrated in FIG. 4A that may be similar or identical in most respects to the system 10 described above, and corresponding reference numbers should be understood as analogous. Those of skill in the art will appreciate that system components described above with reference to FIGS. 1-3B and in the various incorporated references may be used with the embodiments described below within the scope of the present disclosure. The system includes an access cannula 422 (preferably generally straight-line in configuration), which is shown as engaged into a cancellous bone-including region 508 (that may also include marrow and other body material as noted above with reference to FIGS. 2A-3B) of a vertebra 500 via a vertebral pedicle 502 thereof. The distal end 442 of the access cannula 422 has been directed near a target region/site 520 that is generally central within the bone region 508. A portion of the bone region 508 may be at least partially defined by a cortical rim 506 forming a boundary of the anterior vertebral body 504.

The target site 520 may be identified by a physician preparing for a vertebroplasty procedure. Identification of the target site may include generally determining a central location in the cancellous bone portion of the vertebra 500 that will substantially or at least generally support height-restoration and/or structural augmentation that preferably is at least generally symmetrical with respect to the vertebra and particularly with respect to damaged portion(s) thereof. Generally, the target site may be approximately centered within the bone structure. However, the target site is defined more generally as a pre-determined location within a bone structure that may be determined by treating personnel to provide for symmetrical application of force to treat a bone.

Figure 4B:
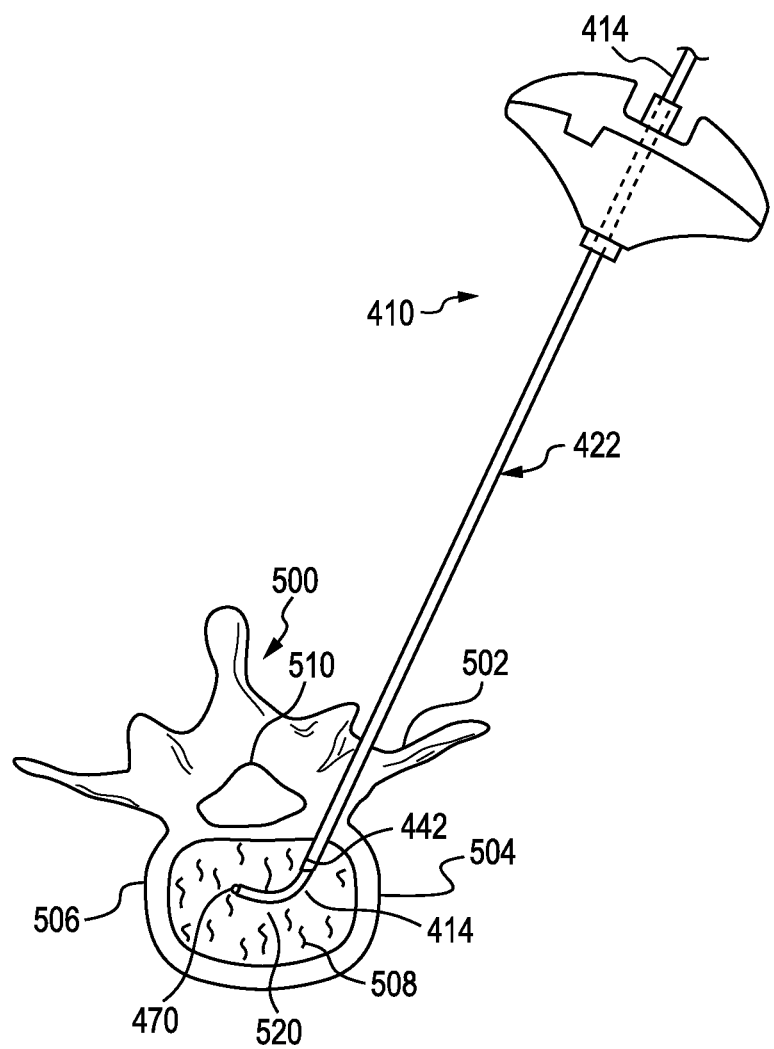

As shown in FIG. 4B, a needle 470 may be directed through the access cannula 422. The needle 470 snugly but slidably extends through an overlying delivery tube 414 that preferably is made a flexible polymer having some columnar strength (e.g., polypropylene, PEEK) that will maintain a patent longitudinal lumen upon withdrawal therefrom of the needle 470. In some embodiments, the needle may be a memory metal with a distal curved length, where the metal needle curve may be constrained to a generally straight-line orientation when constrained during passage through the access cannula. The delivery tube 414 may include at least one radio-opaque marker (e.g., near its distal end) and/or one or more visual indicia near its proximal end providing for user-observation regarding its distal end position relative to the access cannula of the system. The at least one radio-opaque marker includes that the delivery tube may itself be partially or wholly radiopaque. For example, in certain preferred embodiments, a PEEK (or other polymer) delivery tube 414 may be extruded with barium (e.g. barium sulfate) in it, such that some or all of the entire tube is radiopaque, obviating the need for other radio-opaque indicia.

The needle 470 preferably is constructed including a memory metal material having a pre-set curve near its distal end. In this manner, the needle 470 can be deflected to a generally straight orientation while it is being directed through the access cannula 422. The needle and the delivery tube have sufficient length to extend through and be operable beyond the distal end 442 of the access cannula. Thus, as shown in FIG. 4B, in the time and space that the needle 470 is advanced out of the distal end 442 of the access cannula 422, its pre-set curve is re-asserted such that the needle 470 and overlying delivery tube 414 curve into the target region 520. The pre-set curve of the needle 470 may be offset from its distal end sufficiently to provide a generally straight-line portion of the needle distal of its pre-set curve. A proximal-end structure of the needle 470 may include indicia 471 showing the direction of curvature of the pre-set curve (FIG. 4C).

In certain embodiments, a system or kit may include a plurality of needles, each having a different pre-set curve. In this manner, a physician may determine a desirable needle curvature to reach the target region and select an appropriate needle. Each needle may be individually packaged and clearly marked with size and/or curvature, as well as providing other visual indicia of properties of interest to a physician. In use, the physician may determine a desired curvature path between the distal end 442 of the access cannula and the approximate center of the target site (e.g., in the middle of the pre-determined location, which may or may not be generally centered within a bone portion), select a needle including a distal preset curve corresponding to said curvature path from a plurality of needles having different preset curvatures, and insert the selected needle through the delivery tube before directing the assembled needle and overlying tube to the target site.

Figure 4C:
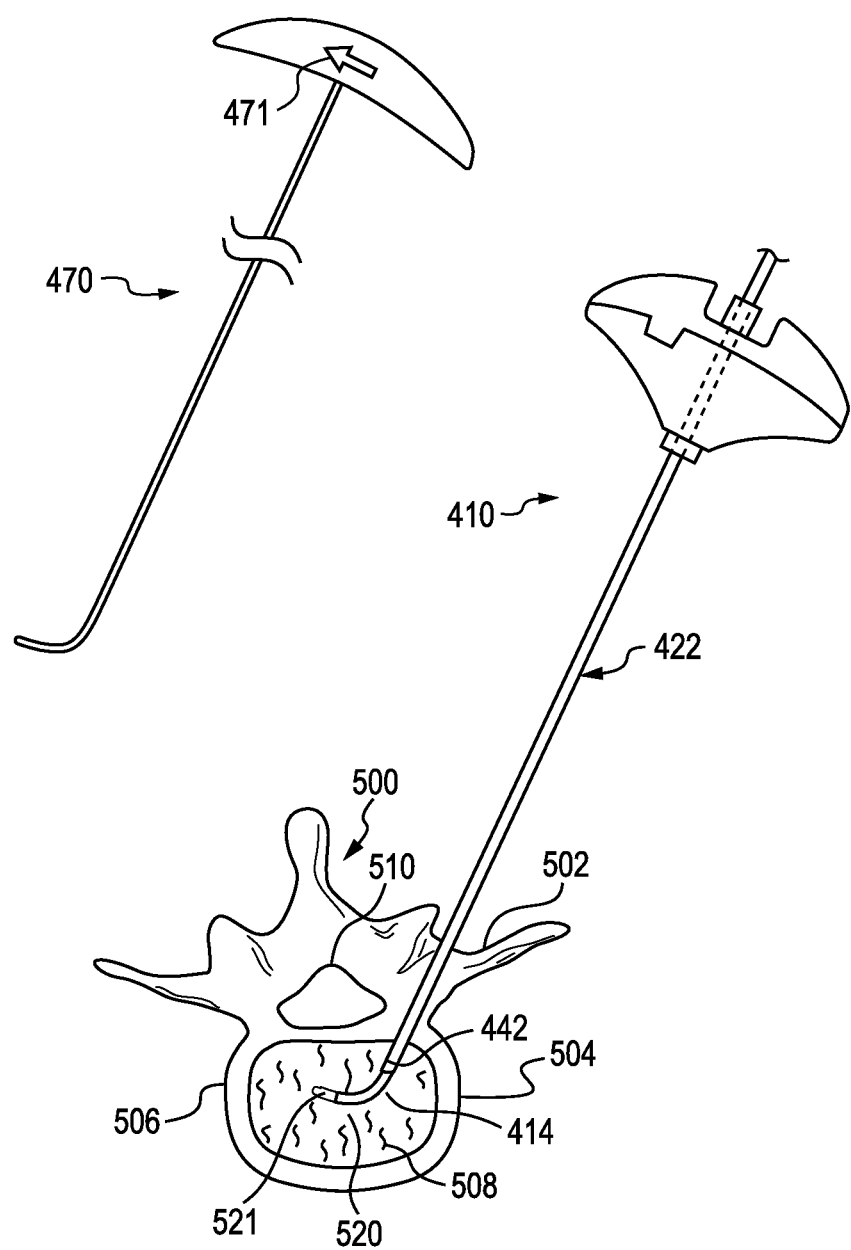
Figure 4D:
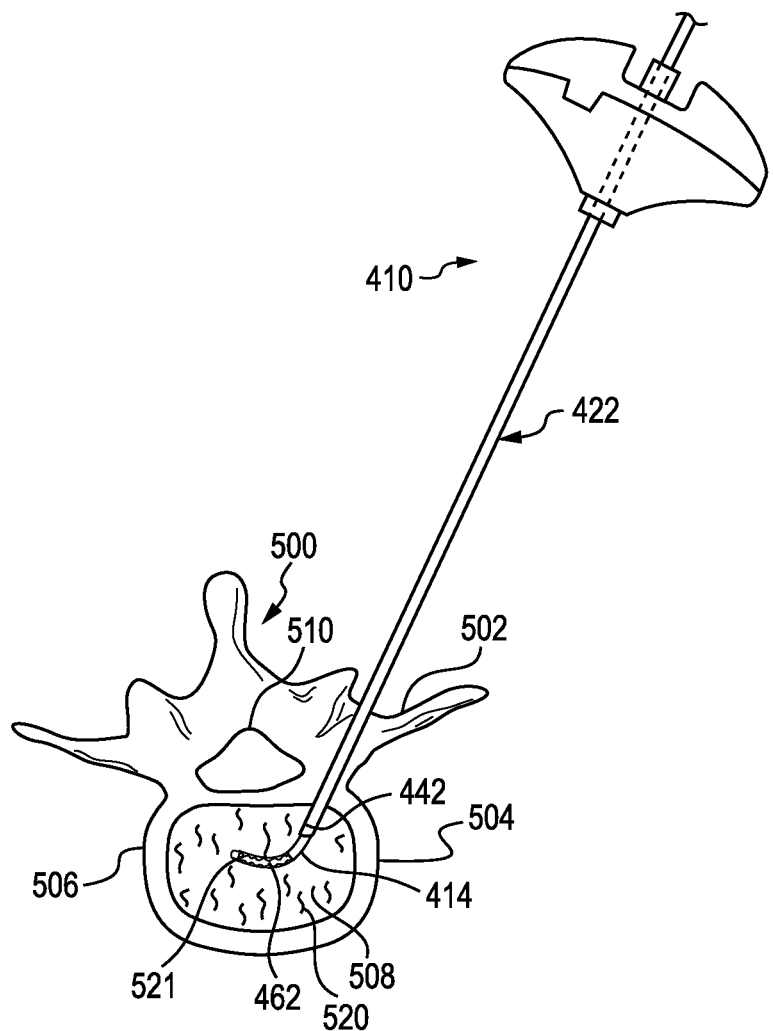

As shown in FIG. 4C, the needle 470 may be withdrawn from the delivery tube 414 (which is shown as slightly retracted from its furthest extension point) after having created a generally tubular path or void 521 in the material of the bone region 508 in the target region 520. Thereafter, as shown in FIG. 4D, a cavity-forming device, which may include a working end embodied as—for example—a distal balloon 462, may be directed into the path 521 formed by the needle 470. A wire or other support structure (not shown) may be provided in the working end/balloon 462 to enhance its trackability and pushability through/into the path 521. In one preferred embodiment of a method, the delivery tube 414 may be extended all the way to the end of the cavity/void formed with the needle 470. Thereafter, the cavity-forming device may be extended through the delivery tube 414 until its working end/balloon 462 contacts the bone at the distal end thereof. This may protect, e.g., a balloon or other distal expandable member of the cavity forming device from external damage during introductory movement and provide for its placement in a desired location and orientation. Thereafter, the delivery tube 414 may be withdrawn sufficiently to allow cavity-forming expansion of the working end/balloon 462 as described below.

Those of skill in the art will appreciate that one or more of the cavity-forming device, working end/balloon 462 thereof, and the delivery tube may include visual indicia (e.g., markings on the user-held end, radio-opaque indicia at or near the distal end) that enable a user to determine the relative positions of those components to perform a method as described. In this or other embodiments, the inner diameter of the delivery tube 414 and/or the external surface(s) of the cavity forming device(s) may be lubriciously coated (e.g., with silicone, PTFE, and/or another lubricious material). For a spinal fusion, the method steps shown in FIG. 4B through FIG. 4H may be replaced or augmented with the method steps illustrated in FIGS. 5A-8D.

Figure 4E:
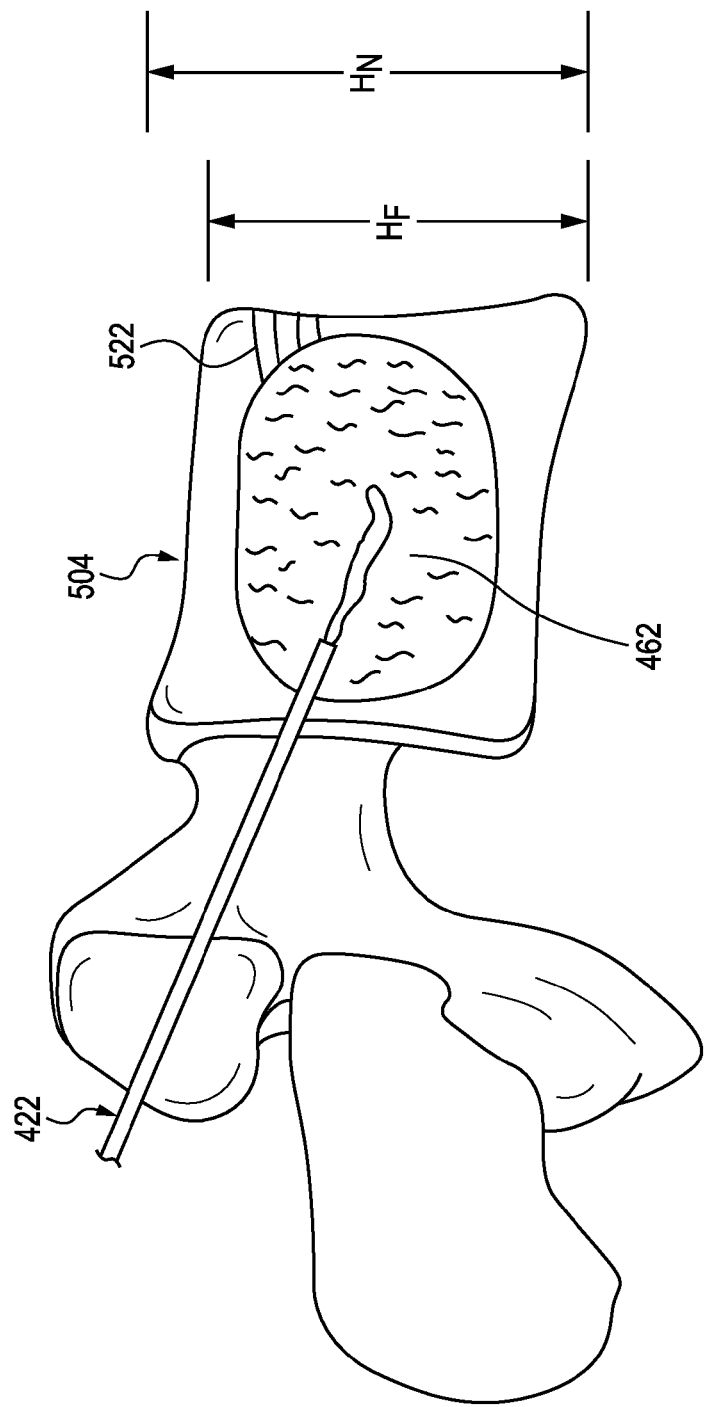
Figure 4F:
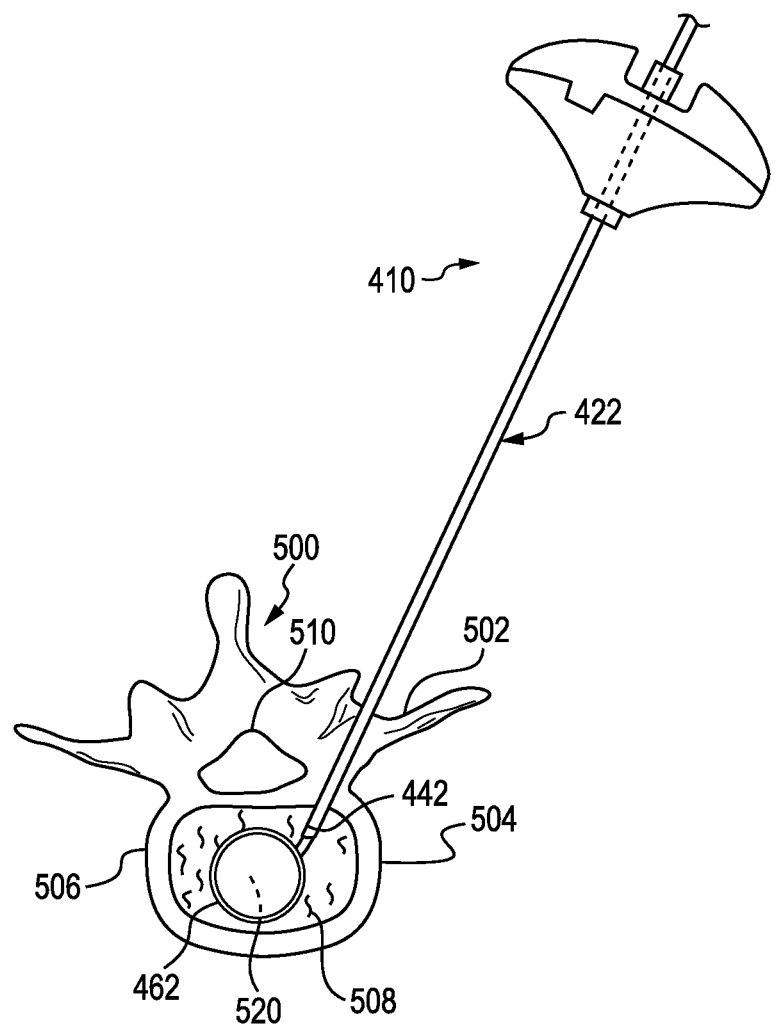
Figure 4G:
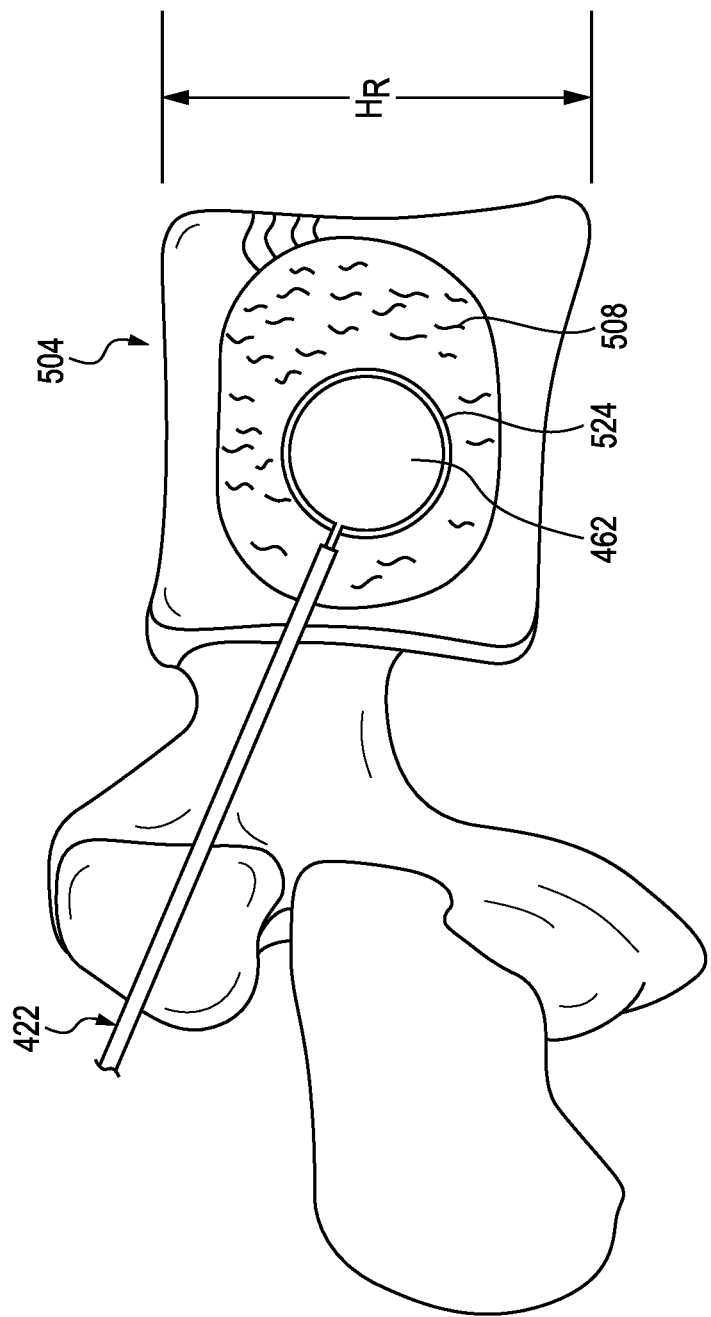

With reference to FIG. 4F, the cavity-forming device may be operated to cause its corresponding working end/balloon 462 to form a (preferably approximately, generally, or substantially centered) cavity/void in the body material-including bone region 508. For example, the working end/balloon 462 may be expanded (e.g., inflated). As best illustrated in FIG. 4G, expansion of the working end/balloon 462 not only forms the cavity, but may also restore or enhance a height of the fractured vertebral body 504. More particularly, a restored height $H_R$ is established that may beneficially approximate the natural height $H_N$. Such a restored height $H_R$ may be the same as, slightly less than, or slightly greater than, the natural height $H_N$ (FIG. 4E); in any event, any restored height $H_R$ will be greater than the fractured height $H_F$ (FIG. 4E). If desired for fluoroscopic visualization, radio-opaque contrast material may be provided into the cavity, internal to or external of the expandable member. Transpedicular access for kyphoplasty at a target site approximately centered in the cancellous bone may not be easily achievable without the curved needle approach of the present disclosure. The limits of patient anatomy, the desirability of minimizing procedure time (for the sake of, e.g., cost and patient health), and the desirability of minimizing patient recovery time all provide for advantages of the present methods and systems.

Figure 4H:
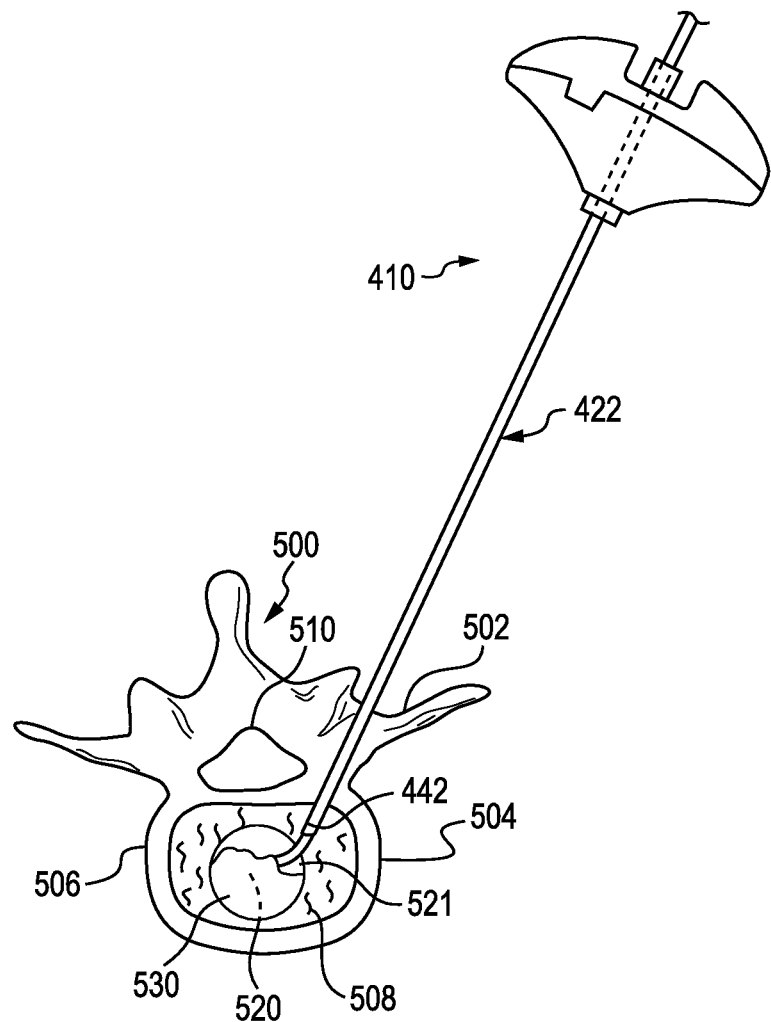

Thereafter, the expandable member's working end/balloon 462 may be withdrawn. Then, as shown in FIG. 4H, curable material 530 may be delivered into the cavity via the delivery tube 414. In this or other embodiments, the curable material may delivered in a more targeted manner via a curved delivery cannula directed though the access cannula into the cavity. In such an embodiment, the delivery tube 414 may be removed as an intermediate step before introducing the curved delivery cannula. Methods and devices for use in introducing curable material via a curved access cannula in a manner useful within the presently disclosed systems and methods are disclosed in U.S. Pat. Nos. 7,713,273; 7,799,035; 8,128,633; and 8,226,657, as well as U.S. Pat. App. Publ. No. 2010/0087828, each of which is incorporated herein by reference in its entirety. It should be understood and appreciated that the "delivery cannula" described therein may include a pre-set curve with structure and function described herein in reference to a "needle." As such the term "needle" as used herein is defined to include a delivery cannula that has an internal lumen dimensioned and oriented for delivering curable material. This definition may therefore, in some embodiments, provide a needle that is embodied as a delivery cannula, while—in other embodiments—provide a needle separate from a delivery cannula. Specifically, in the methods described above, and those described below, a delivery cannula, which may be embodied as an AVAflex® Curved Vertebral Augmentation Needle (CareFusion Corp., San Diego, Calif.), can be used. In this manner the curable material will be directed through the lumen of the cannula into the space created by an expandable device. The methods described herein are less invasive and less traumatic than those described in the art (e.g., in U.S. Pat. No. 6,558,390 to Cragg).

Figure 5A:
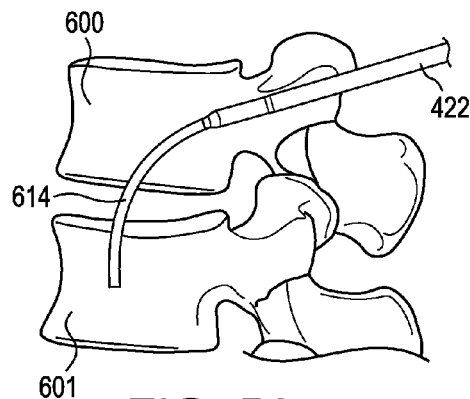
FIGS. 5A-5C show steps of a kyphoplasty method for augmenting and/or fusing adjacent vertebrae using a generally non-compliant balloon inflated in and across the vertebrae.
Figure 5B:
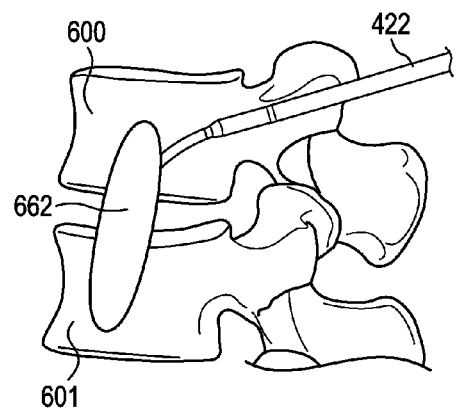
Figure 5C:
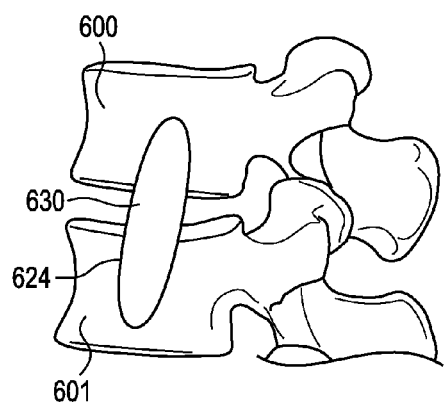

One method of spinal fusion using a kyphoplasty procedure is illustrated with reference to FIGS. 5A-5C. A first vertebra 600 and a second, immediately adjacent, vertebra 601 are shown diagrammatically in FIG. 5A. The diagrammatic illustration in this and the following figures omits musculature, intervertebral disc material, and other surrounding viscera. It shows a side plan view of method embodiments, each of which is described with reference to a transpedicular insertion of an access cannula 422 (e.g., similar or identical to that shown in the top view of FIG. 4H; method steps herein are also applicable within the scope of the present application to parapedicular procedures). In each of the following embodiments, the cortical bone between the viewer and the area being treated is not shown (including the portion of the transverse process between the viewer and the pedicle being penetrated by an access cannula), but it should be understood that the voids formed and filled will be surrounded around the lateral sides by the cortical bone of the vertebrae's outer circumferential surfaces. In FIG. 5A, a curved needle is introduced into and through the first vertebra 600. The needle is disposed within/through an overlying introducer tube 614 and so is not visible in FIG. 5A, but may be embodied as a curved needle such as a needle 470 referenced above (e.g., a memory metal delivery cannula embodied as an AVAflex® Curved Vertebral Augmentation Needle (CareFusion Corp., San Diego, Calif.)), or a different solid-body needle or stylet with a predetermined curvature that will provide a desired path). Access through the cortical bone of the vertebral pedicle is provided via an access cannula 422.

The curved needle within overlying introducer tube 614 provides sufficient mechanical force along a pre-determined curve to form a channel through a portion of the body of the first vertebra 600, out through its upper or lower (as illustrated) face, and into the body of the second vertebra 601. The needle is withdrawn, and a balloon 662 is inserted through the lumen of the introducer tube 614, which may ease passage of the balloon along the desired channel/track to the targeted region. Then, the introducer tube 614 is withdrawn at least sufficiently to expose the balloon and allow balloon expansion, and the balloon 662 is inflated to form a cavity across the vertebra 600, 601, as illustrated in FIG. 5B. The balloon 662 may be removed, and the cavity 624 then filled with curable material (e.g., PMMA, other bone cement, or other appropriate biocompatible material providing desirable curability and post-curing mechanical strength) to form a cured material body 630. This filling step may be done using a needle such as AVAflex® or another appropriate cement-introducing device. As shown in FIG. 5C, the cured material body 630 forms a rigid fusing mass across the two adjacent vertebrae 600, 601.

Figure 5D:
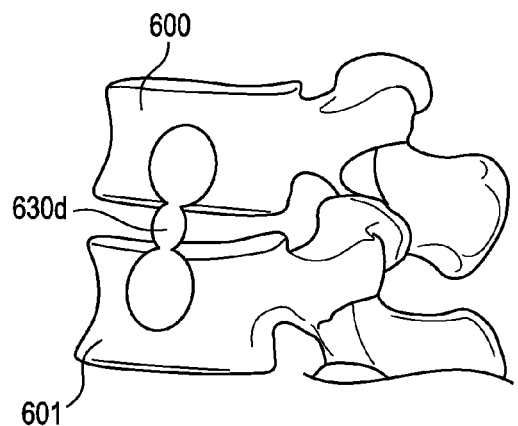
FIG. 5D shows a spinal fusion similar to the method of FIGS. 5A-5C, but having been implemented with a generally compliant kyphoplasty balloon method.

It should be appreciated that this can be done via the opposite-side pedicle also to form another spinal fusion cured material body. Alternatively, in the steps associated with FIG. 5A, one or more differently curved needle(s) can be used via the same access cannula to form one or more other tracks for balloon-inflation and formation of cured material body(ies). Stated differently, this same set of method steps may be repeated at a different left/right orientation, superior/inferior (i.e., cephalic/caudal), and/or different anterior/posterior (i.e., ventral/dorsal) orientation via the same access cannula entry, via the other pedicle of the same or a different vertebra, or elsewhere. The body 630 shown in FIG. 5C is formed by using a generally non-compliant balloon that—upon inflation under pressure—assumes a sausage-like shape to form that shape of a cavity/void in the vertebrae 600, 601 and generally displaces bone material rather than just conforming to the bone. It should be appreciated that the generally non-compliant balloon can, in certain embodiments, be configured to assume any appropriate inflated shape/outer geometry, as most medically appropriate for the target site. However, in other methods, a compliant or semi-compliant balloon may be used that will expand to a greater degree where it contacts cancellous bone in the vertebrae 600, 601, but to a lesser degree where it contacts the denser cortical bone around the margins of the vertebrae 600, 601, such that—at its typical operating pressure—the compliant or semi-compliant balloon will conform at least somewhat after initial displacement of bone. FIG. 5D shows such an embodiment, where a compliant balloon has been used to form a cured material mass 630d across the vertebrae 600, 601, the contours of which reflect the differing density/resistance of the material contacted by the balloon during expansion to form a cavity, filled to form a cured-material spinal bridge mass 630d. In the methods described with reference to FIGS. 5A-5D, those of skill in the art will appreciate that the balloon used is elongate with a proximal-distal length greater than its diameter. However, other balloon shapes (e.g., spherical, spheroid, etc.) may be used.

Figure 6A:
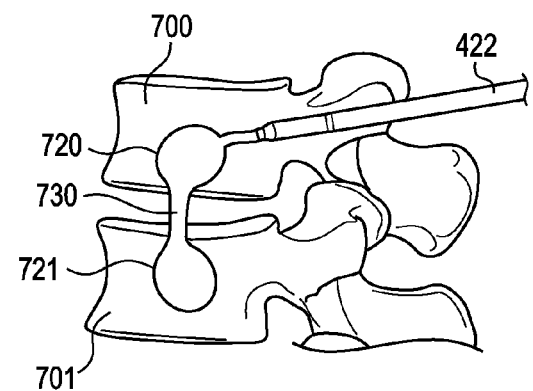
FIGS. 6A-6B show spinal augmentation and/or fusion structures that may be implemented by serial inflation, deflation, repositioning, and re-inflation of a smaller balloon within (or within and across) adjacent vertebrae.
Figure 6B:
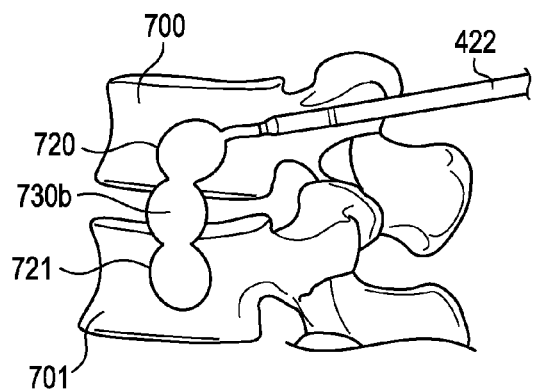

FIGS. 6A and 6B illustrate other embodiments of cured material spinal-fusion masses that can be formed using adapted versions of the method described with reference to FIGS. 5A-5C. The balloon embodiment shown and described is generally spheroid, but other balloon geometries may be used, as most appropriate for the bone structure being treated. In the embodiment of FIG. 6A, the method steps for creating a channel (described above) have been implemented, and a spheroid balloon used to create a first cavity 721 in the second vertebra 701 and a second cavity 720 in the first vertebra 700. Thereafter, a continuous spinal-fusing mass of curable (now cured) material 730 was introduced, filling and connecting the second and first cavities, forming the dumbbell-shaped mass illustrated. This mass 730 is anchored in the first vertebra 700 and in the second vertebra 701, with an intermediate portion that forms the fusion between those vertebrae. In an alternative non-fusion technique, each of the cavities 720, 721 may be filled for augmentation of the vertebrae 700, 701 without forming the intermediate mass 730. In FIG. 6B, the spheroid balloon was inflated to create an intervening/intermediate void between the first cavity 721 in the second vertebra 701 and the second cavity 720 in the first vertebra 700 (e.g., within and across the endplates and intervening tissue, the latter of which is not shown). The resulting continuous spinal-fusing mass of curable (now cured) material 730b is shown as providing a stable bridge across the vertebrae 700, 701 between the respective cured material masses therein.

Figure 7:
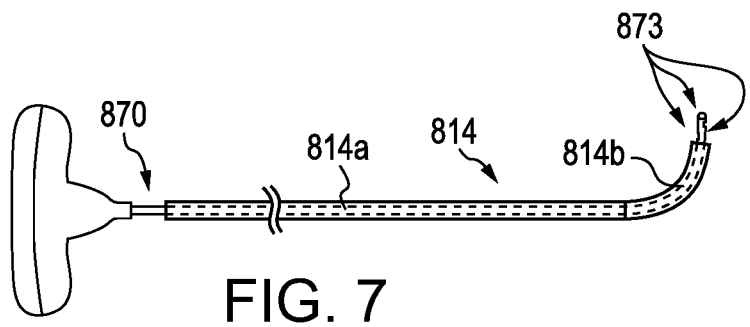
FIG. 7 shows an introducer device.

Another method for forming a spinal fusion is described with reference to FIGS. 7-7D. FIG. 7 shows a two-piece introducer tube 814, disposed snugly over the outside of a curved needle 870. The tube 814 is substantially continuous in all contours, except that it is formed of two distinct lengths: a proximal length 814a and a distal tube length 814b. The distal tube length 814b generally will be significantly shorter than the proximal tube length 814a. In certain embodiments, the distal tube length 814b may be about one-half inch (about 1.3 cm) to about 3 inches (about 7.6 cm) long. In one embodiment, the distal tube length 814b may be about 1.5 inches (about 3.8 cm) long. As illustrated in FIG. 7, the needle 870 includes a pre-set curve and its distal tip includes at least one opening 873 dimensioned to permit passage therethrough of curable material such as, for example, bone cement for vertebroplasty and related procedures. In the illustrated embodiment three openings, including a distal-tip-facing opening and two side openings are provided to facilitate multidirectional delivery of curable material. Like the other introducer tube embodiments described herein, the tube 814 preferably is made of or at least including a limited-flexibility polymer providing some columnar strength (e.g., polypropylene, PEEK) that will maintain a patent longitudinal lumen upon withdrawal therefrom of the needle 870. This differs significantly from prior art methods of a detachable metal member that is injected/directed into and across vertebral bodies and then detached and left in place to form a fusion bridge, as those methods do not use an underlying needle and do not incorporate the elegant and efficient methods disclosed here of incorporating vertebral augmentation with curable material.

Figure 7A:
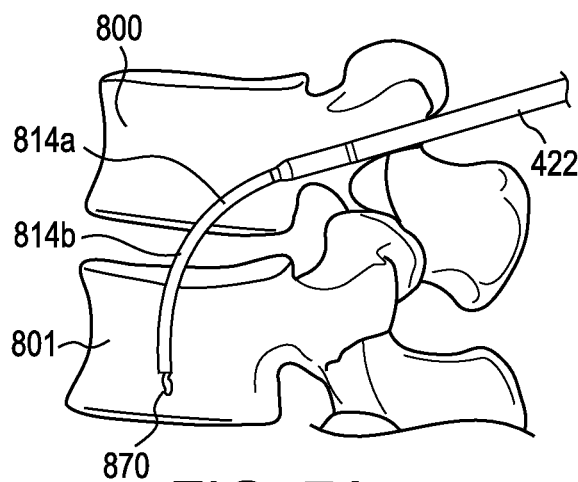
FIGS. 7A-7D show a method of performing fusion between adjacent vertebrae.

As in the method described above with reference to FIG. 5A, a first vertebra 800 and a second, immediately adjacent, vertebra 801 are shown diagrammatically in FIG. 7A. In FIG. 7A, the curved needle 870 is introduced into and through the first vertebra 800. The needle 870 is disposed within/through the overlying introducer tube 814. Access through the cortical bone of the vertebral pedicle is provided via an access cannula 422 in the manner described above for other vertebroplasty and kyphoplasty methods.

Figure 7B:
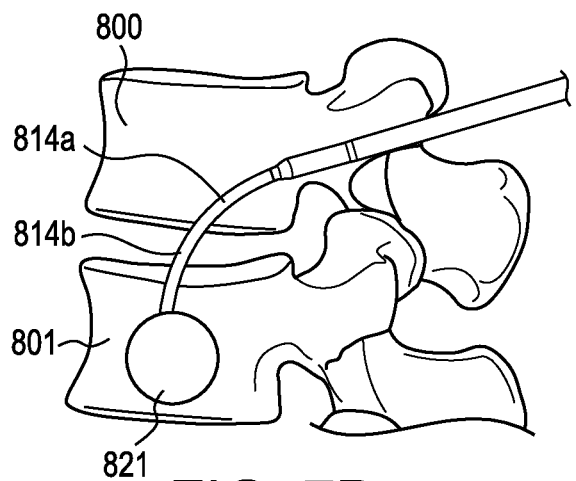

The curved needle 870 within the overlying tube 814 provides sufficient mechanical force along its pre-determined curve to form a channel through a portion of the body of the first vertebra 800, out through its upper or lower (as illustrated) face, and into the body of the second vertebra 801. In this manner, the tube 814, and particularly the distal tube length 814b bridges across the vertebrae 800, 801. (In other embodiments, an initial track and intravertebral voids may have been formed using a balloon method as described above with reference to FIGS. 5A-5B or to FIG. 6A, before the present needle/tube assembly 870/814 is introduced, through a common access cannula after removal of balloon (s)). Next, as shown in FIG. 7B, curable material 830 is injected out through the opening(s) 873 of the needle 870 to permeate and displace cancellous bone within the body of the second vertebra 801, forming a first mass 821 in the second vertebra 801.

Figure 7C:
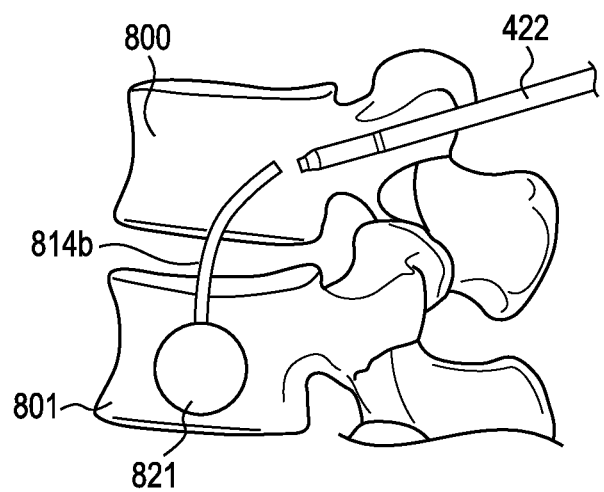
Figure 7D:
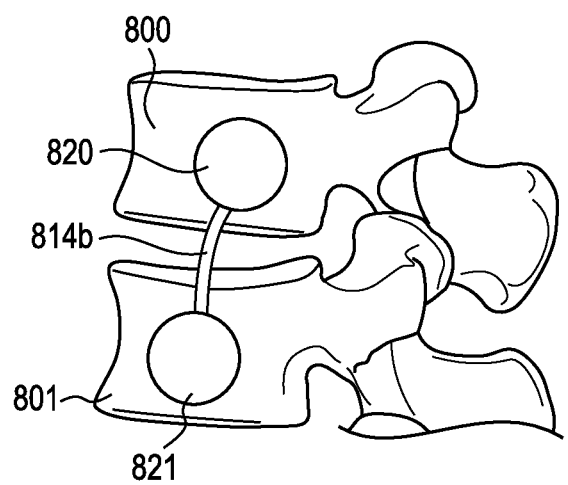

Thereafter, as shown in FIG. 7C, the needle 870 is withdrawn while still injecting curable material into the distal tube length 814b. At the same time, the proximal tube length 814a is retracted—leaving the distal tube length 814b in place where it bridges the intervertebral gap (across the disc—not shown) between the first and second vertebrae 800, 801. The injection of material continues as the needle 870 is withdrawn past the proximal end of the distal tube length 814b. Thus, curable material 830 is injected out through the opening(s) 873 of the needle 870 to permeate and displace cancellous bone within the body of the first vertebra 800, forming a second mass 820 in the first vertebra 800, shown in FIG. 7D. As shown in FIG. 7D, the needle 870 and the access cannula 422 are removed.

The resulting structure is a dumbbell-shaped spinal fusion structure with first and second curable/cured material masses 821, 820 joined by an intermediate curable/cured mass body that is columnarly reinforced across the vertebrae 800, 801, where the end masses may surround a portion of the left-behind tube length 814b. This same set of method steps may be repeated at a different left/right orientation and/or different anterior/posterior orientation via the same access cannula entry, via the other pedicle of the same or a different vertebra, or elsewhere. For the steps described with reference to FIGS. 7B-7D, after the initial channel is formed by the needle 870 and overlying tube 814, the needle 870 may be withdrawn and a differently-curved needle or other injection device may be used to direct curable material into the vertebrae 800, 801. A solid curved stylet or other device may be used to cannulate and form a larger void for receiving curable material, as is known in the art of vertebroplasty.

Alternatively, one or more balloons may be used to form one or both voids that will be filled by the masses 820, 821, by modifying this method according to the method described above, which those of skill in the art will appreciate with reference to the presently disclosed teachings, particularly with reference to the methods described with reference to FIG. 6A, except that the balloon(s) would be introduced and inflated on either end of the distal tube length 814b, then removed and a needle or other device for delivering curable material provided and actuated.

Methods for treating a plurality of adjacent vertebrae are described with reference to FIGS. 8A-8D. The methods generically and diagrammatically shown in FIGS. 8A-8D may be executed like the methods described above: a needle (not shown) disposed through an overlying tube 914 is directed via an access cannula 422 through a pedicle of a first vertebra 900. The needle and overlying tube are directed down through the cancellous bone of the body of the first vertebra 900, out through the inferior (caudal) end plate of the first vertebra 900 and through the superior (cephalic) end plate of the second vertebra 901 into the cancellous bone of the body of that vertebra. This establishes a path, track, or channel for further method steps as described above and below.

Figure 8A:
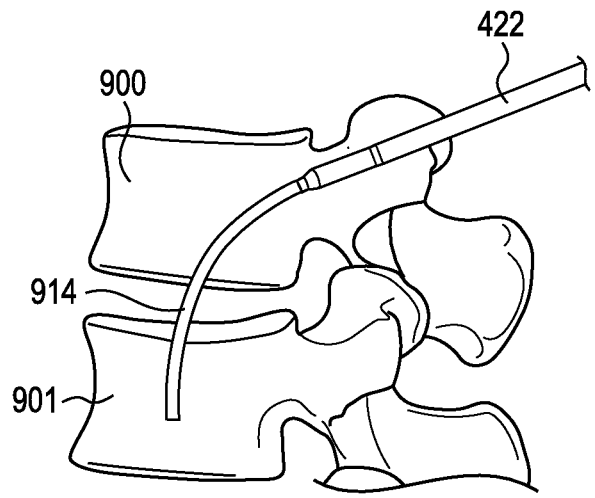
FIGS. 8A-8D show methods of forming fusion between adjacent vertebrae.
Figure 8B:
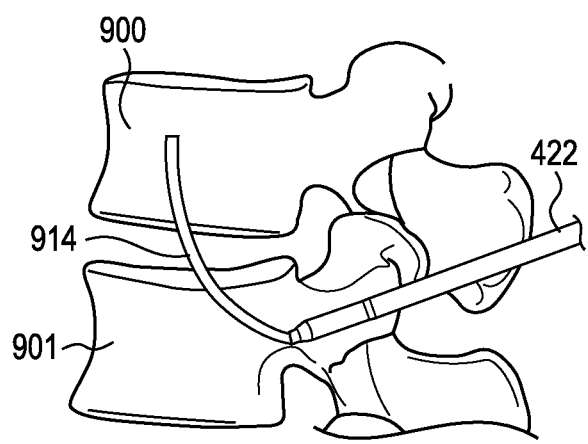

The method generically and diagrammatically shown in FIG. 8B is modified somewhat from that described above, by being top/bottom reversed: a needle (not shown) disposed through an overlying tube 914 is directed via an access cannula 422 through a pedicle of a first vertebra 901. The precurved end of the needle and overlying tube are directed up through the cancellous bone of the body of the first vertebra 901, out through the superior (cephalic) end plate of the first vertebra 901 and through the inferior (caudal) end plate of the second vertebra 900 into the cancellous bone of the body of that vertebra. This establishes a path, track, or channel for execution of further method steps as described above and below.

Each of the methods described above refers to fusing two adjacent vertebrae, but it should be appreciated that those methods may be used and/or altered to augment the adjacent vertebrae without forming a fusion body across and between them. It should also be appreciated that the presently-disclosed methods can be used to fuse three or more adjacent vertebrae. Modification by extension of those methods is described with reference to FIGS. 8C-8D. These figures each show three adjacent vertebrae as first (900), second (901), and third (903) vertebrae to be fused according to a method (or combined steps from methods) of the present disclosure.

Figure 8C:
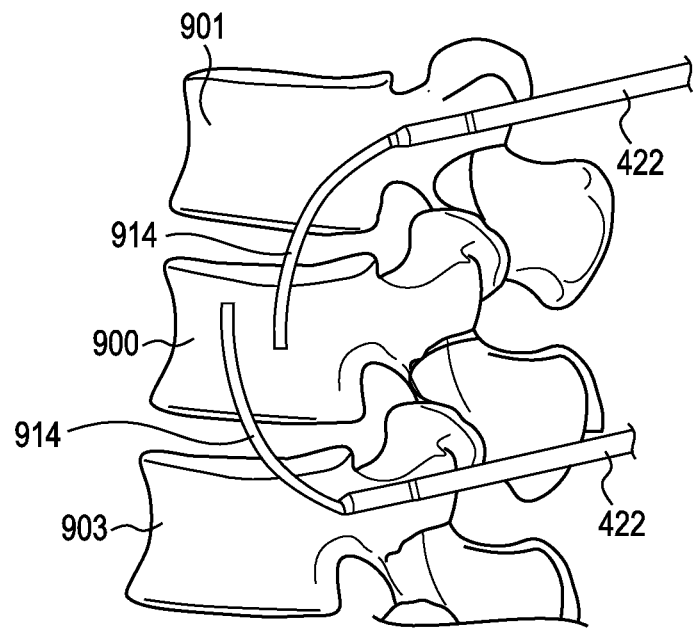

In the method depicted in FIG. 8C, a dual-entry approach is shown. Common reference numbers are used in this narrative, but it should be appreciated that the same or different individual needle(s), access cannula(s), tube(s), etc. may be used. Specifically, the upper or the lower portion of the method may be done first followed by the other of the upper or lower portion of the method, using the same tool elements. Or, one or more duplicate tool elements may be used in succession (or simultaneously) during a procedure in keeping with the methods of FIGS. 8C and/or 8D.

In FIG. 8C, a needle (not shown) disposed through an overlying tube 914 is directed via an access cannula 422 through a pedicle of the second vertebra 901. The needle and overlying tube are directed down through the cancellous bone of the body of the second vertebra 901, out through the inferior (caudal) end plate of the second vertebra 901 and through the superior (cephalic) end plate of the first vertebra 900 into the cancellous bone of the body of that vertebra to form an upper track/channel for spinal fusion. For the lower portion of the method of FIG. 8C, a needle (not shown) disposed through an overlying tube 914 is directed via an access cannula 422 through a pedicle of the third vertebra 903. The precurved end of the needle and overlying tube are directed up through the cancellous bone of the body of the third vertebra 903, out through the superior (cephalic) end plate of the third vertebra 903, and then through the inferior (caudal) end plate of the first vertebra 900 into the cancellous bone of the body of that vertebra to form a lower track/channel for spinal fusion. Thereafter one of the other methods (or any combination thereof) described above may be completed for forming a spinal fusion across each of the upper and lower track.

In the method of FIG. 8C, the upper and lower portions are shown as being offset from each other along the anterior/posterior (ventral/dorsal) axis. Those of skill in the art should appreciate that the tracks formed may overlap or merge, they may be offset from each other at various angles and along any axis. They may be formed by access along same-side or opposite-side (left versus right) pedicles, and may be repeated to form multiple spinal fusions in different locations between the subject vertebrae, all in keeping with the scope of the present disclosure. Treating personnel (e.g., orthopedic surgeon, radiologist, etc.) may adjust and modify the methods described herein to locate spinal fusions along particular axes and/or at particular locations relative to the vertebrae being treated in any of the methods described herein.

Figure 8D:
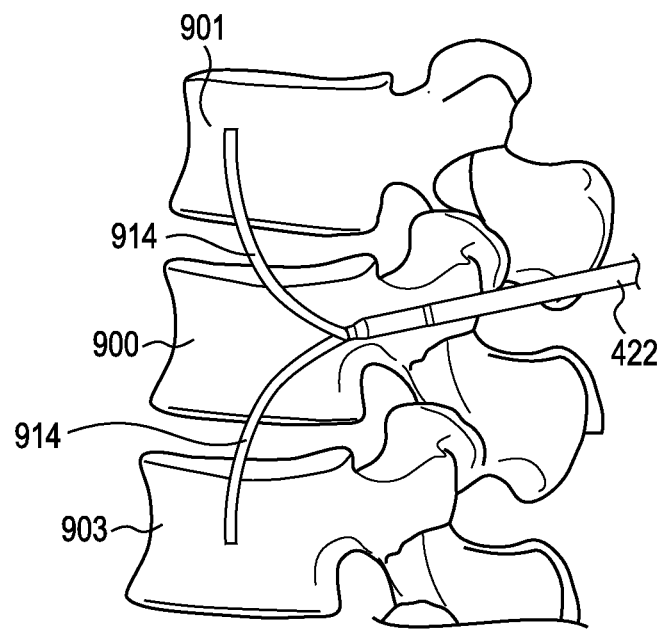

A different method, using an access location in a single central vertebra to fuse it to superior and inferior adjacent vertebrae, is described here with reference to FIG. 8D. In FIG. 8D, a needle (not shown) disposed through an overlying tube 914 is directed via an access cannula 422 through a pedicle of the first vertebra 900. The needle and overlying tube are directed down through the cancellous bone of the body of the first vertebra 900, out through the inferior (caudal) end plate of the first vertebra 900 and through the superior (cephalic) end plate of the third vertebra 903 into the cancellous bone of the body of that vertebra to form a lower track/channel for spinal fusion (like FIG. 8A). For the upper portion of the method of FIG. 8D, a needle (not shown) disposed through an overlying tube 914 is directed via an access cannula 422 through the pedicle of the first vertebra 900. The precurved end of the needle and overlying tube are directed up through the cancellous bone of the body of the first vertebra 900, out through the superior (cephalic) end plate of the first vertebra 900, and then through the inferior (caudal) end plate of the second vertebra 901 into the cancellous bone of the body of that vertebra to form an upper track/channel for spinal fusion (like FIG. 8B). Thereafter one of the other methods (or any combination thereof) described above may be completed for forming a curable-material-enhanced spinal fusion across each of the upper and lower track.

In the illustration for the method of FIG. 8D, the upper and lower portions are shown as being offset from each other along the anterior/posterior (ventral/dorsal) axis. Those of skill in the art should appreciate that the upper and lower tracks formed may align along a chosen axis, or they may be offset from each other at various angles and along any axis. They may be formed by access along same-side or opposite-side (left versus right) pedicles (in a dual-access-point variation of this single-vertebra-access method), and may be repeated to form multiple spinal fusions in different locations between the subject vertebrae, all in keeping with the scope of the present disclosure.

In each of the embodiments of FIGS. 8A-8D, the structure shown as tube 914 may instead be embodied as a tubular or solid-body memory material that will be released as an implant to form a fusion structure between adjacent vertebrae. Those of skill in the art will appreciate that tubular or solid-body memory material may include, for example, Nitinol or other biocompatible memory-metal or memory-polymer materials known in the medical arts. Appropriate materials will assume a shape-set, but will allow sufficient straightening for passage/introduction through the access cannula 422 (much like the tubular memory metal body of the aforementioned AVAflex® needle). The relative and absolute dimensions contemplated here are those known in the art for diameters of vertebroplasty and kyphoplasty tools. In one preferred embodiment that will be fully understood with reference to the present application, the tube 914 may be embodied as a memory-metal tube configured like the releasable distal tube length 814b, where it can be introduced as an overlay of an underlying needle or stylet that is then withdrawn, leaving the tube 914 in place as a fusing bridge across adjacent vertebrae.

Certain of the presently described methods may include and/or may benefit from improvements to methods and devices disclosed in U.S. Pat. App. Pub. No. 2012/0239047 and U.S. patent application Ser. No. 14/050,017, filed Oct. 9, 2013, each of which is incorporated by reference herein in its entirety.

Those of skill in the art will appreciate that embodiments not expressly illustrated herein may be practiced within the scope of the claims, including that features described herein for different embodiments, and in different claims, may be combined with each other and/or with currently-known or future-developed technologies while remaining within the scope of the claims. This includes providing the apparatus, a kit, and/or instructions (spoken, written, or otherwise) for conducting the inventive methods herein described. Although specific terms are employed herein, they are used in a generic and descriptive sense only and not for purposes of limitation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment.

We claim:

1. A method for augmenting and/or fusing adjacent vertebrae, the method comprising:
    directing an access cannula into a first vertebra;
    directing a needle into the first vertebra, wherein a distal portion of the needle extends through and beyond a distal end of the access cannula within a body portion of the first vertebra;
    further extending the distal portion of the needle through an upper or lower surface of the first vertebra and into a body portion of a second vertebra, thereby forming a channel across and between the body portions of the first and second vertebrae;
    directing a balloon within the channel; and
    expanding the balloon within the channel with sufficient force to enlarge the channel to form a void within the body portion of at least one of the first and second vertebrae.

2. The method of claim 1, further comprising:
    deflating and retracting the balloon; and
    directing curable material into the void.

3. The method of claim 1, further comprising:
    directing the balloon within the channel to a first target region within the body portion of the second vertebra; and
    expanding the balloon within the channel with sufficient force to form the void within the second vertebra.

4. The method of claim 3, further comprising:
    deflating and retracting the balloon within the second vertebra; and
    directing curable material through the access cannula in the first vertebra and into the void within the second vertebra.

5. The method of claim 4, further comprising
    directing the balloon within the channel to a second target region, the second target region being within the first vertebra; and
    expanding the balloon with sufficient force to form a second void, the second void being within the first vertebra;
    deflating and retracting the balloon; and
    directing curable material through the access cannula in the first vertebra and into the second void within the first vertebra.

6. The method of claim 5, further comprising directing curable material within the channel to form a fusion body coupling the curable material in the body portions of the first and second vertebrae.

7. The method of claim 1, wherein the second vertebra comprises a fractured height and a restored height greater than the fractured height, the method further comprising:
    directing the balloon within the channel and to a target region within the body portion of the second vertebra; and
    expanding the balloon within the second vertebra with sufficient force to alter the second vertebra from the fractured height to the restored height.

8. The method of claim 7, further comprising the step of directing curable material into the body portion of the second vertebra while the second vertebra is at the restored height.

9. The method of claim 8, further comprising deflating and retracting the balloon after the step of directing curable material.

10. The method of claim 1, further comprising removing material from the body portion of the second vertebra.

11. The method of claim 1, further comprising:
    coating the balloon with lubricious material; and
    thereafter, directing the balloon within the channel and the body portion of the first vertebra and into the body portion of the second vertebra.

12. The method of claim 1, further comprising:
    directing a delivery tube overlying the needle through the upper or lower surface of the first vertebra and into the body portion of the second vertebra with the delivery tube comprising a distal tube length releasable from a proximal tube length; and
    releasing the distal tube length from the proximal tube length within the channel.

13. The method of claim 12, wherein the released distal tube length is positioned to bridge an intervertebral gap between the first and second vertebrae.

14. The method of claim 12, further comprising retracting the needle while directing curable material within the released distal tube length.

15. The method of claim 12, wherein the void is within the body portion of one of the first and second vertebrae, the method further comprising:
    deflating and retracting the balloon within the channel; and
    directing curable material into the void within the one of the first and second vertebrae to form a first mass.

16. The method of claim 15, further comprising:
    directing the balloon into the body portion of another one of the first and second vertebrae; and
    expanding the balloon with sufficient force to form a second void, the second void being within the other one of the first and second vertebrae;
    deflating and retracting the balloon; and
    directing curable material into the second void to form a second mass, the second mass being within the other one of the first and second vertebrae,
    wherein the released distal tube length joins the first and second masses.

17. The method of claim 12, wherein the distal tube length comprises a polymer configured to maintain a patent longitudinal lumen upon removal of the needle from the delivery tube.

18. The method of claim 1, further comprising:
directing a two-piece introducer through the upper or lower surface of the first vertebra and into the body portion of the second vertebra with the two-piece introducer comprising a distal length releasable from a proximal length; and
releasing the distal length within the channel to bridge an intervertebral gap between the first and second vertebrae.

* * * * *